(12) United States Patent
Kilgard et al.

(10) Patent No.: US 9,265,660 B2
(45) Date of Patent: *Feb. 23, 2016

(54) METHODS, SYSTEMS, AND DEVICES FOR TREATING TINNITUS WITH VNS PAIRING

(71) Applicants: MicroTransponder, Inc., Austin, TX (US); The Board of Regents, The University of Texas System, Austin, TX (US)

(72) Inventors: Michael P. Kilgard, Richardson, TX (US); Navzer Engineer, Plano, TX (US); David Michael Pierce, Plano, TX (US)

(73) Assignees: MICROTRANSPONDER, INC., Austin, TX (US); THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,893

(22) Filed: Jul. 3, 2013

(65) Prior Publication Data

US 2013/0289653 A1    Oct. 31, 2013

Related U.S. Application Data

(60) Division of application No. 13/673,764, filed on Nov. 9, 2012, now Pat. No. 8,666,501, which is a continuation-in-part of application No. 13/095,570, filed on Apr. 27, 2011, now Pat. No. 9,089,703, which (Continued)

(51) Int. Cl.
*A61N 1/00* (2006.01)
*A61F 11/00* (2006.01)
(Continued)

(52) U.S. Cl.
CPC ............... *A61F 11/00* (2013.01); *A61B 5/128* (2013.01); *A61N 1/361* (2013.01); *A61N 1/36032* (2013.01); *A61N 1/36053* (2013.01); *A61N 1/36167* (2013.01); *A61N 1/36171* (2013.01); *A61N 1/36178* (2013.01); *A61N 1/37235* (2013.01); *G09B 23/28* (2013.01); *H04R 25/75* (2013.01); *A61N 1/0551* (2013.01);

(Continued)

(58) Field of Classification Search
CPC ........... A61N 1/37235; A61N 1/36053; A61N 1/361; A61N 1/36171; A61N 1/36178; A61N 1/36167; A61N 1/36032; A61N 1/0551; A61N 1/36092; A61N 1/36132; A61N 1/37247
USPC ........................................................ 607/55–57
See application file for complete search history.

(56) References Cited

U.S. PATENT DOCUMENTS

| 4,475,427 A | 10/1984 | Starkey |
| 5,325,872 A | 7/1994 | Westermann |

(Continued)

*Primary Examiner* — Michael Kahelin
*Assistant Examiner* — Mallika D Fairchild
(74) *Attorney, Agent, or Firm* — Hauptman Ham, LLP

(57) ABSTRACT

A method of treating tinnitus comprising measuring a patient's hearing, determining the patient's hearing loss and the patient's tinnitus frequency using the measurements of the patient's hearing, programming a clinical controller with the measurements of the patient's hearing, selecting a plurality of therapeutic tones, where the therapeutic tones are selected to be at least a half-octave above or below of the patient's tinnitus frequency, setting an appropriate volume for each of the plurality of tones, repetitively playing each of the plurality of therapeutic tones, and pairing a vagus nerve stimulation pulse train with each playing of a therapeutic tone, thereby reducing the patient's perception of tinnitus.

26 Claims, 19 Drawing Sheets

Related U.S. Application Data is a continuation-in-part of application No. 12/485,040, filed on Jun. 15, 2009, now Pat. No. 9,089,707.

(60) Provisional application No. 61/699,470, filed on Sep. 11, 2012, provisional application No. 61/614,369, filed on Mar. 22, 2012, provisional application No. 61/598,185, filed on Feb. 13, 2012, provisional application No. 61/558,287, filed on Nov. 10, 2011, provisional application No. 61/328,621, filed on Apr. 27, 2010, provisional application No. 61/077,648, filed on Jul. 2, 2008, provisional application No. 61/078,954, filed on Jul. 8, 2008, provisional application No. 61/086,116, filed on Aug. 4, 2008, provisional application No. 61/149,387, filed on Feb. 3, 2009.

(51) Int. Cl.

| | | |
|---|---|---|
| *A61N 1/36* | (2006.01) | |
| *A61B 5/12* | (2006.01) | |
| *G09B 23/28* | (2006.01) | |
| *H04R 25/00* | (2006.01) | |
| *A61N 1/05* | (2006.01) | |
| *A61N 1/372* | (2006.01) | |

(52) U.S. Cl.
CPC ......... *A61N1/36092* (2013.01); *A61N 1/36132* (2013.01); *A61N 1/37247* (2013.01)

(56) References Cited

U.S. PATENT DOCUMENTS

| | | |
|---|---|---|
| 5,403,262 A | 4/1995 | Gooch |
| 6,610,019 B2 * | 8/2003 | Choy .......................... 600/559 |
| 6,816,599 B2 | 11/2004 | Thiede |
| 2006/0018497 A1 | 1/2006 | Kornagel |
| 2007/0027504 A1 | 2/2007 | Barrett |
| 2007/0179534 A1 | 8/2007 | Firlik |

* cited by examiner

FIG. 23

METHODS, SYSTEMS, AND DEVICES FOR TREATING TINNITUS WITH VNS PAIRING

CROSS-REFERENCE TO RELATED APPLICATIONS

This application claims the benefit of U.S. Provisional Patent Application No. 61/699,470, filed Sep. 11, 2012, U.S. Provisional Patent Application No. 61/614,369, filed Mar. 22, 2012, U.S. Provisional Patent Application No. 61/598,185, filed Feb. 13, 2012, and U.S. Provisional Patent Application No. 61/558,287, filed Nov. 10, 2011. This application is also a Continuation-In-Part of U.S. patent application Ser. No. 13/095,570, filed Apr. 27, 2011, which claims the benefit of U.S. Provisional Patent Application No. 61/328,621, filed Apr. 27, 2010 and which is a Continuation-In-Part of U.S. patent application Ser. No. 12/485,040, filed Jun. 15, 2009, which claims the benefit of: U.S. Provisional Patent Application No. 61/077,648, filed Jul. 2, 2008; U.S. Provisional Patent Application No. 61/078,954, filed Jul. 8, 2008; U.S. Provisional Patent Application No. 61/086,116, filed Aug. 4, 2008; and U.S. Provisional Patent Application No. 61/149,387, filed Feb. 3, 2009. All of these applications are incorporated herein by reference as if reproduced in their entirety.

RELATED APPLICATIONS

The present application is a division of application Ser. No. 13/673,764, filed Nov. 9, 2012, entitled METHODS, SYSTEMS, AND DEVICES FOR TREATING TINNITUS WITH VNS PAIRING, the disclosure of which is hereby incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Tinnitus is characterized by an auditory sensation in the absence of external sound. Approximately 12 million individuals in the United States have some degree of tinnitus. About 5 million of these sufferers have severe tinnitus that interferes with their daily activities and their quality of life. In fact, severe tinnitus can lead to depression and other mental health challenges that severely affect the patient and the patient's family members. Therapies such as masking, sound therapy, electrical stimulation, and drugs have shown some benefit. Unfortunately, these treatments are non-specific and are insufficient to reverse the brain changes that cause tinnitus. Therefore, treatment of tinnitus remains a significant unmet need.

Numerous therapies have been used to treat or alleviate the symptoms of tinnitus. For example, pharmaceutical therapies such as antidepressants, anti-anxiety medications, as well as other medicinal compounds have been attempted. Neurostimulation techniques including transcranial magnetic stimulation and cortical stimulation have been used to alleviate symptoms. Sound has been used in several ways, including masking therapy auditory exposure and frequency discrimination training.

U.S. Patent Application Publication 2007/0027504 (Barrett) describes a system for treating tinnitus using vagus nerve stimulation. A patient's vagus nerve was stimulated as the patient experienced tinnitus symptoms to temporarily alleviate the symptoms. No audible tones are specifically presented or paired in Barrett's therapy.

U.S. Pat. No. 6,990,377 (Gliner) describes a therapy to treat visual impairments. The therapy includes presenting various types of visual stimuli in conjunction with stimulation of the visual cortex. The therapy described in Gliner does not control the timing relationship of the stimuli and the stimulation.

U.S. Patent Application Publication 2007/1079534 (Firlik) describes a therapy having patient interactive cortical stimulation and/or drug therapy. The therapy has patients performing tasks, detecting patient characteristics, and modifying the stimulation depending on the detected patient characteristics. The therapy described in Firlik does not control the timing relationship between the tasks and the cortical stimulation.

It is common in the prior art to suggest that stimulation of the cortex, the deep brain, the cranial nerves, and the peripheral nerves are somehow equivalent or interchangeable to produce therapeutic effects. Despite these blanket statements, stimulation at different parts of the nervous system is not equivalent. It is generally understood that the vagus nerve is a nerve that performs unique functions through the release of a wide array of neuromodulators throughout the brain. To generate certain kinds of plasticity, the timing of the stimulation of the vagus nerve is critical in producing specific therapeutic effects.

U.S. Pat. No. 6,104,956 (Naritoku) is representative of work done using vagus nerve stimulation (VNS) to treat a variety of disorders, including epilepsy, traumatic brain injury, and memory impairment. The VNS is delivered without any other therapy. To improve memory consolidation, VNS is delivered several minutes after a learning experience. Memory consolidation is unrelated to the present therapy for treating tinnitus.

SUMMARY

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

In an embodiment the disclosure includes a method of treating tinnitus comprising measuring a patient's hearing, determining the patient's hearing loss and the patient's tinnitus frequency using the measurements of the patient's hearing, programming a clinical controller with the measurements of the patient's hearing, selecting a plurality of therapeutic tones, where the therapeutic tones are selected to be at least a half-octave above or below of the patient's tinnitus frequency, setting an appropriate volume for each of the plurality of tones, repetitively playing each of the plurality of therapeutic tones, and pairing a vagus nerve stimulation pulse train with each playing of a therapeutic tone, thereby reducing the patient's perception of tinnitus.

In another embodiment the disclosure includes a system for treating tinnitus comprising a clinical controller executing tinnitus therapy software, a VNS implantable pulse generator (IPG) in communication with the clinical controller and receiving stimulation signals from the clinical controller, a VNS lead connected to the VNS IPG, a VNS electrode connected to the VNS lead and receiving stimulation signals through the VNS lead from the VNS IPG, and headphones connected to the clinical controller, wherein the clinical controller plays selected sound files through the headphones while sending stimulation signals to the VNS IPG such that the sound files may be heard by a patient while a stimulation pulse train at the VNS electrode causes the patient's vagus nerve to be stimulated.

In yet another embodiment the disclosure includes a method of treating tinnitus comprising measuring a patient's hearing, determining the patient's hearing loss and the patient's tinnitus frequency using the measurements of the patient's hearing, programming a clinical controller with the measurements of the patient's hearing, selecting a plurality of therapeutic tones where the therapeutic tones are selected to be at least a half-octave above or below of the patient's tinnitus frequency, generating sound files by shaping the selected therapeutic tones using a ramp function, modulating the sound files with phase information that simulates a sound source location, setting an appropriate volume for each of the plurality of tones, repetitively playing each of the plurality of therapeutic tones, and pairing a vagus nerve stimulation pulse train with each playing of a therapeutic tone, thereby reducing the patient's perception of tinnitus.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

FIG. 23 is a screen shot of stimulation parameter setting; and

DETAILED DESCRIPTION

Figure 1A:
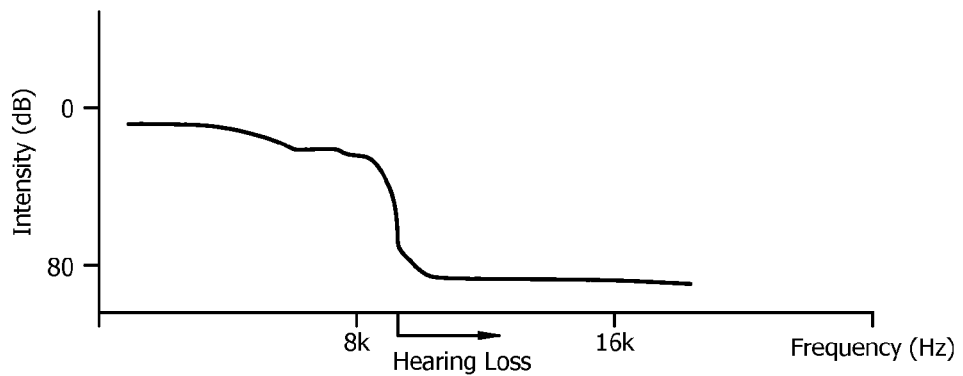
FIGS. 1A, 1B, and 1C are graphs depicting aspects of a patient's hearing.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents. The present application describes several embodiments, and none of the statements below should be taken as limiting the claims generally.

Where block diagrams have been used to illustrate the embodiments, it should be recognized that the physical location where described functions are performed are not necessarily represented by the blocks. Part of a function may be performed in one location while another part of the same function is performed at a distinct location. Multiple functions may be performed at the same location. In a functional block diagram, a single line may represent a connection, in general, or a communicable connection, particularly in the presence of a double line, which may represent a power connection. In either case, a connection may be tangible, as in a wire, or radiated, as in near-field communication. An arrow may typically represent the direction of communication or power although should not be taken as limiting the direction of connected flow.

Repeatedly pairing a range of non-tinnitus frequency sounds with VNS reduces the perception of tinnitus sounds in a patient with tinnitus. No one ever before recognized that playing repeated VNS paired sounds could reduce symptoms of tinnitus.

A common cause of hearing loss that leads to tinnitus is cochlear damage from noise trauma. Elevated synchronous spontaneous activity in the central auditory system may account for the tinnitus percept that arises following hearing loss. As a result, some neurons in the auditory cortex no longer receive their normal input. These neurons start responding to adjacent frequencies, and therefore a population of neurons starts firing spontaneously and synchronously. This pathological activity is thought to give rise to the tinnitus sensation. Based on these considerations, we developed an approach to reduce the tinnitus percept by redistributing the frequencies along the auditory tonotopic axis, thus reducing the responsiveness of neurons that had too much input. Our approach pairs selected tone presentations other than the tinnitus frequency with simultaneous stimulation of the vagus nerve to induce a redistribution of the distorted auditory cortical frequency map observed in tinnitus. This approach seems to alleviate the presumed behavioral and neurophysiological correlations of tinnitus in a rat model of the disease.

The mechanism of our therapy may be referred to as repeated paired training. A repeated paired training is defined as follows:

A "training" may be defined as a discrete event in time that has a starting point and a stopping point. In the case of tinnitus therapy, a training may be a brief sound, such as a tone with a distinct frequency.

A training may be defined as "paired" when a discrete vagus nerve stimulation pulse train, having a starting point and a stopping point, occurs during a training. This requires that the training and VNS start and stop in a manner that links the two together in time. When both the training and VNS have stopped, there may follow a period when there is neither training nor VNS. This non-training period allows the brain to perceive the next event as a separate discrete event. The mechanism of therapy takes advantage of the fact that the brain can distinguish between two discrete events close together in time.

A "repeated paired training" may be defined as a recurring sequence of paired trainings. The mechanism of our therapy is the cumulative effect of repeated paired trainings.

The vagus nerve is composed of somatic and visceral afferents (e.g., inward conducting nerve fibers which convey impulses toward a nerve center such as the brain or spinal cord) and efferents (e.g., outward conducting nerve fibers which convey impulses to an effector to stimulate it and produce activity). 80% of the fibers in the vagus nerve are afferent fibers; the rest are efferent. The vast majority of vagal nerve fibers are C fibers, with the majority being visceral afferents having cell bodies lying in masses or ganglia in the skull. The central projections terminate largely in the nucleus of the solitary tract which sends fibers to various regions of the brain (e.g., the hypothalamus, thalamus, locus ceruleus, and amygdala); others continue to the medial reticular formation of the medulla, the cerebellum, the nucleus cuneatus, and other regions. Afferents activate both ascending and descending pathways.

The vagus nerve may be contacted at any point along its length or one of its branches. For instance, stimulating or sensing electrodes may be located directly on, or close to, the left and/or right vagus nerve(s) in a cervical location. Alternatively, the vagus nerve could be stimulated at a near-diaphragmatic location (e.g., supra-diaphragmatic or sub-diaphragmatic).

Stimulation of the vagus nerve may beneficially activate one or more of the gustatory pathways, olfactory pathways, pro-inflammatory or anti-inflammatory pathways, respiratory pathways, cardiac pathways, baroreceptor pathways, and the somatosensory pathways, causing a response of neural activity in various areas of the brain. Vagus nerve stimulation may also affect neurotransmitter pathways such as noradrenergic, serotoninergic, dopaminergic catecholaminergic, GABAergic, opioidergic and cholinergic pathways similarly. Neural activating circuits may include the circuit of Papez, the mesolimbic pathway, the mesocortical pathway or the nigrostriatal pathway. The effect of such responsive effect on the brain tissue may be excitatory or inhibitory and may potentiate acute and/or long-term changes in neuronal activity.

The afferent vagus nerve feeds in the Nucleus Tractus Solitarius which in turn feeds into several deep brain nuclei including nucleus basalis and locus ceruleus. Each activation of the vagus nerve results in a release of acetylcholine from the nucleus basalis and norepinephrine from the amygdala and locus ceruleus. These neurotransmitters influence the cortex and other parts of the brain. The context of this release of neuromodulators defines the effects.

The release of the neuromodulators resulting from activation of the vagus nerve during a paired sensory event generates plasticity in the cortex that is specific to the sensory event. The pairing effectively tells the brain what to learn. Activation of the vagus nerve during a sensory event such as a sound or sound sequence generates plasticity in the auditory cortex that is specific to the sound or sound sequence because the perception of the sound coincides with the release of neuromodulators in the auditory cortex. Activation of the vagus nerve during a motion generates specific plasticity in the motor cortex, again because the action and released neuromodulators coincide in the motor cortex. The conjunction of these simultaneous activations generates specific plasticity with a very brief window, less than eight seconds for tinnitus.

Until our experiments, the synergy of these activations was unappreciated. Presenting a sensory event at the same time as activation of the vagus nerve has an effect on the area of the cortex related to the sensory event. Timing a sensory event with vagus nerve stimulation activates the appropriate parts of the brain. The described tinnitus therapy has been developed using these principles and tested clinically.

The tinnitus therapy includes a controlled-timing vagus nerve stimulation. The vagus nerve may be stimulated using effective methods, such as direct electrical stimulation. Direct electrical stimulation of the vagus nerve may be performed using an implantable vagus nerve stimulator or a percutaneous vagus nerve stimulator to provide electrical pulses to an electrode close to the vagus nerve tissue. Other methods of stimulating the vagus nerve could be used as appropriate, as long as the timing of the vagus nerve stimulation can be controlled. In accordance with an embodiment of the therapy, an implantable vagus nerve stimulation device may be implanted in the patient. Alternatively, a percutaneous lead could be attached to an electrode at the vagus nerve through the patient's skin to provide stimulation of the vagus nerve. The necessary surgery may be performed in advance of the actual therapy, so the tissue has time to heal.

Figure 1B:
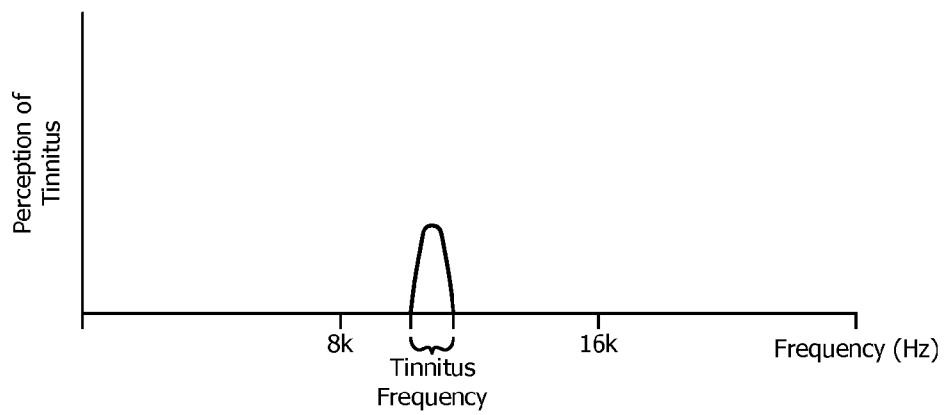
Figure 1C:
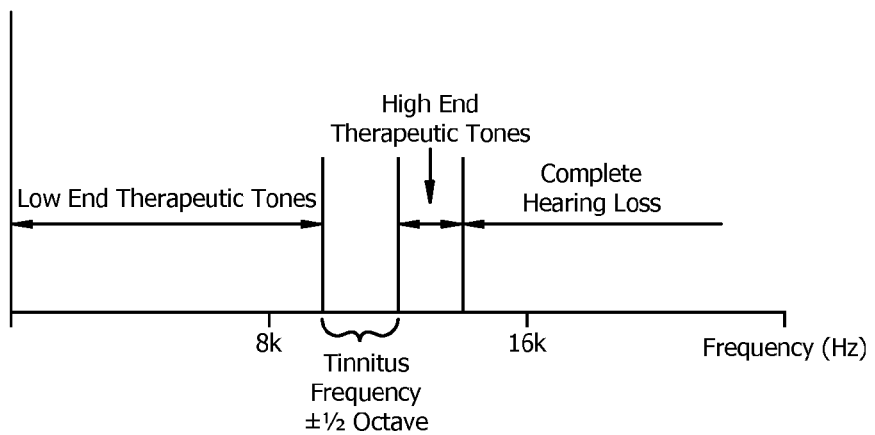

When the therapy is ready to begin, the patient's hearing and tinnitus symptoms are assessed. An audiogram may be generated by an audiologist to characterize the patient's hearing loss. Tinnitus pitch matching may be done to measure one or more frequencies at which the patient is experiencing tinnitus. One patient's hearing is depicted in FIG. 1A, and the patient's tinnitus symptoms is depicted in FIG. 1B. A range of therapeutic tones for the patient is depicted in FIG. 1C. Because the hearing and symptoms of every patient is individual and unique, the hearing loss, tinnitus symptoms, and range of therapeutic tones may differ from those shown.

Using the knowledge of the patient's hearing loss and the frequency or frequencies that characterize a patient's tinnitus symptoms, the clinician selects a set of therapeutic tones at frequencies the patient can hear, not including the patient's tinnitus frequencies. The clinician may select tones at frequencies ranging from 170 hertz (Hz) to 16 kilohertz (kHz) and adjust the intensity accordingly. In accordance with an embodiment, 25 therapeutic frequencies may be selected. The distribution of frequencies may be based on Mel scales.

In accordance with an embodiment, therapeutic tones may be generated using pure sine wave tones with a sampling rate of 44,100 Hz. This relatively high sampling rate ensures the tones are pure. The sampling rate should be at least twice as high as the highest frequency being used as a tone.

Figure 2:
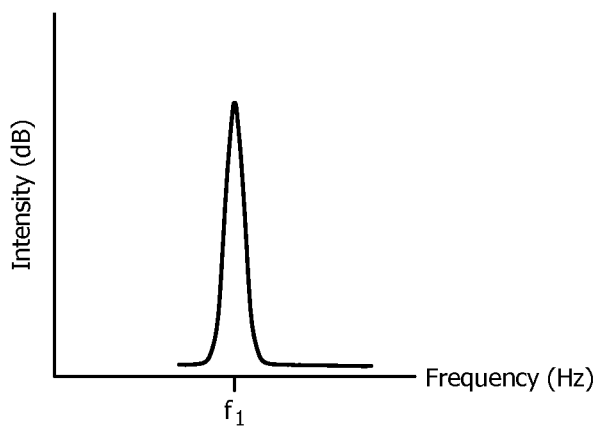
FIG. 2 depicts a pure tone.

Using the data generated by the audiogram, a set of sound files may be generated for the therapy. A therapeutic tone may be a pure tone, as shown in FIG. 2. A pure tone may be defined as a presentation of a single frequency that exhibits no harmonic distortions. For the purpose of this therapy, a tone may be said to be pure when the ratio of the single frequency to any other frequency (harmonics, ambient noise, etc.) is 20:1 or greater. A tone may be sufficiently pure when only the single frequency can be discerned by a patient.

Figure 3A:
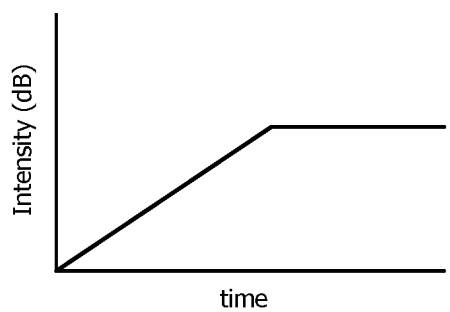
FIG. 3A depicts an up ramp tone.
Figure 3B:
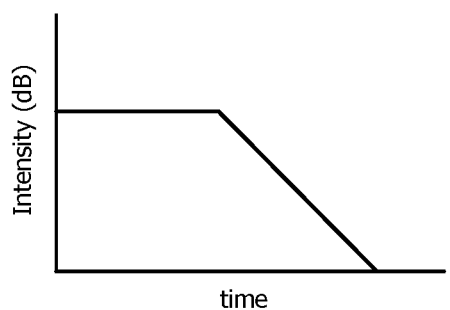
FIG. 3B depicts a down ramp tone.

Because a pure tone as a sine wave has an abrupt start and stop, the presentation of a pure tone can seem to include unpleasant pops at the beginning and end of the tone. To prevent this phenomenon, a 4-10 millisecond ramp can be introduced to modulate the start and stop. A ramp up, as shown in FIG. 3A, may be used at the start of the tone and a ramp down, as shown in FIG. 3B, may be used before the stop.

The brain may struggle when presented with a stereo in-phase, equal amplitude pure tone, because the lack of location information in this simple tone makes it impossible for the mind to place the source of the sound in space. To make the tone presentation more natural, to give the sound an apparent location in space both in terms of direction and distance, the therapy may include phase and amplitude adjustments between the left and right headphone speakers, so that a tone is heard by the patient as existing at a specific location in space.

Encoding multiple locations which are applied randomly to the tones may be important, because training an association between a specific tone and a specific location may have adverse consequences. We do not want to train the patient to pay attention to only one location or tone, but rather have the VNS occur at random locations and frequencies.

A variety of models can be used to encode locations and environments. In accordance with one embodiment, a rectangular room, with a drop ceiling, carpet, four walls, and microphones at specific locations provides the model environment. The model environment simulates the echoes, delays, and absorption at the microphone. Output is determined at seventeen locations in each of the two rooms. A second environment may be one where all walls completely absorb sound, which is effectively the same as being outdoors.

Figure 4:
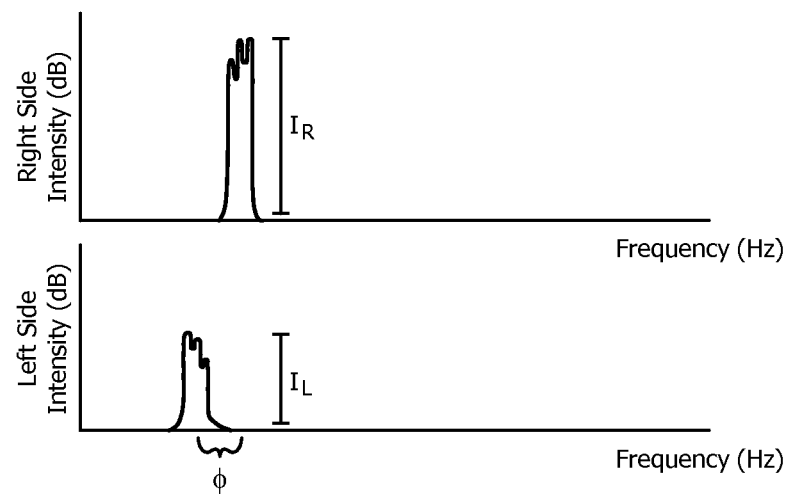
FIG. 4 depicts location encoded sounds.

For the 34 locations in the two rooms, a set of impulse functions is generated. Each of these impulse functions is multiplied with a sine wave of a selected frequency to create a complex tone waveform for that location, distance, room, and tone, as shown in FIG. 4. To create the sense of a tone coming from a specific location in space, the sound for the right ear is given an intensity $I_R$ and the sound for the left ear is given an intensity $I_L$ and the left and right sounds are separated with a time delay ($\phi$). By changing the intensity values and the time delay, the sounds will seem to be coming from different locations in space, in different environments.

The clinician may test the volume setting of the device before the therapy begins. The volume of the tones should be audible and comfortable to the patient. Because a pure tone necessarily has a louder output than a complex tone waveform, pure tones may be used to check the volume settings.

In accordance with an embodiment, each of the 36 (34 locations+right and left pure tones) complex tone waveforms are multiplied with each of the 25 selected therapeutic tones to provide 900 left and right sound files. These sound files may be stored on the clinical controller. The clinical controller includes a soundcard connected to stereo headphones. When the clinical controller plays a sound file, the soundcard converts the sound file to an output that is received by the stereo headphones and converted to audible sound. Because each soundcard and headphone has a unique frequency response, they may introduce variables that may need to be compensated. Typically, the therapy is conducted at 80 decibels (dB) or less. Headphones and soundcards may introduce harmonics and distortions volumes higher than 80 dB. A patient may need to be able to hear a reasonable number (at least two) of tones at 80 dB.

The tinnitus therapy may be summarized as follows: The patient has an implantable VNS device implanted so that it can provide stimulation to the patient's vagus nerve on command. An audiologist generates an audiogram for the patient. The tinnitus frequency or frequencies are determined. The frequency of each therapeutic sound or tone is selected by the audiologist or clinician based on the tinnitus frequency. The apparent location of each tone is established by the audiologist, clinician, or an automated process that provides a suitable selection of perceived tone locations. The tone may be shaped by a ramp. The clinician goes through a software setup procedure, and a clinical setup is performed.

The intensity of each therapeutic tone is set. Typically the intensity is assigned an initial value. A clinician may check with the patient to determine if the initial intensity settings are appropriate and may change the intensity of one or more tones accordingly. The intensity may be calculated from the audiogram data. Feedback loops may be incorporated for automatic control of intensity. From the intensity, the voltage required to produce the tone is determined. Typically this is performed by software, automatically.

An audiogram is generated by an audiologist and provided as input to the software. The audiogram measures the hearing loss at each frequency, measured in dB Hearing Loss (HL). The data from the audiogram is then converted from a hearing loss measure into dB Sound Pressure Level (SPL). A sound check may be performed. The tinnitus therapy, once set up by the clinician, may be performed by the patient at home. The software may give options to the clinician to set-up the therapy for home use, in particular to allow the patient to deliver the therapy to themselves, at home, while not allowing the patient to change the parameters of the therapy.

The software is designed to deliver the therapeutic tones and the vagus nerve stimulation to the patient at the same time. In accordance with an embodiment, the therapeutic tones are each about 500 milliseconds in duration and the vagus nerve stimulation pulse train is about 500 milliseconds. In accordance with an embodiment, a therapy session may include about 300 therapeutic tones paired with about 300 vagus nerve stimulations. In accordance with an embodiment, a therapy regime may include about six weeks of therapy sessions, provided about five times per week. The tinnitus therapy includes a number of variables that may be changed, as appropriate.

Figure 5A:
FIGS. 5A, 5B, and 5C are graphs of stimulation timing relationships.
Figure 5B:
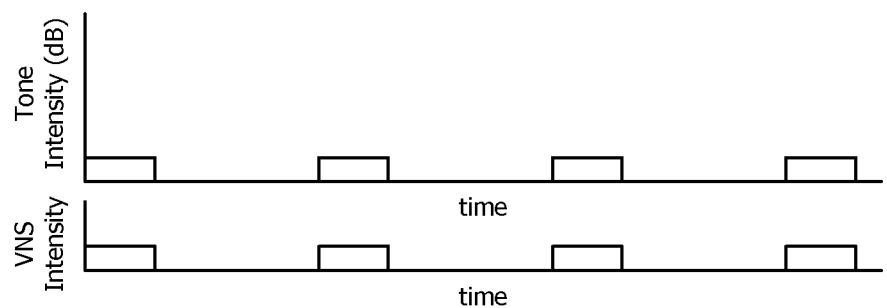
Figure 5C:
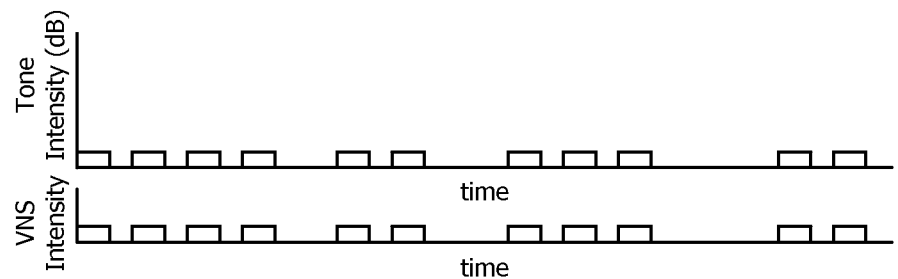

In accordance with an embodiment, the therapeutic tones are about 500 milliseconds. The duration of the therapeutic tones may be made longer or shorter. FIG. 5A depicts a relative timing diagram for the tone and vagus nerve stimulation pulse train. FIG. 5B depicts a relative timing diagram for a plurality of tones and vagus nerve stimulation pulse trains. FIG. 5C depicts a relative timing diagram for randomly spaced tones and vagus nerve stimulation pulse trains.

In accordance with an embodiment, twenty-five therapeutic tones are selected by the clinician. The twenty-five tones may be selected at regular intervals through frequencies that can be heard by the patient, except the frequencies that characterize the patient's tinnitus or within a half-octave of the tinnitus frequencies. More or less tones may be selected as appropriate. The vagus nerve stimulation pulse trains delivered to the patient are 500 milliseconds in duration. The duration of the vagus nerve stimulation pulse trains may be longer or shorter as appropriate. The vagus nerve stimulation pulse trains delivered to the patient are about 0.8 milliamps. The intensity of the stimulation may be more or less than 0.8 milliamps, as appropriate. The intensity of the tones being delivered to the patient should be set to a level that is comfortable for the patient. Depending on a patient's hearing loss, the intensity of the tones may be set to a normal level or a higher level. In accordance with an embodiment, the therapeutic tones and vagus nerve stimulations are delivered at the same time, within a few milliseconds. It may be appropriate to begin the therapeutic tones earlier than the vagus nerve stimulation or after the vagus nerve stimulation. The tones are typically delivered at 30-second intervals. The intervals may be changed as appropriate. The clinician may select 25 therapeutic tones. More or less tones may be selected, as appropriate. The session will typically include 300 therapeutic tones paired with vagus nerve stimulations. More or less tones may be delivered during a session, as appropriate. The therapy may include 20 sessions. More or less sessions may be given, as appropriate. The sessions may be provided daily. Sessions may be provided more or less often, as appropriate.

By controlling the phase of the tones in a stereo environment, the tones may be given the subjective attribute of apparent location. The locations of one or more tones may be varied, as appropriate. In accordance with an embodiment, various randomizations may be introduced. The selection of tones, from the therapeutic tones, for delivery to the patient, may be randomized. The timing of the tone delivery may be randomized. In accordance with an embodiment, the tones have a 50% chance of being delivered at 15 seconds intervals, so that on average, the tones are delivered thirty seconds apart. By controlling the phase of the tones in a stereo environment, the tones may be given the subjective attribute of apparent location. This location of tones may be randomized.

A variety of systems and devices may be used to implement the tinnitus therapy. A percutaneous lead may be used to stimulate the vagus nerve. Because of the risk of infection is increased with a percutaneous lead, the duration of the therapy delivered will necessarily be shorter (less than six weeks) than is possible with an implanted lead.

Figure 6:
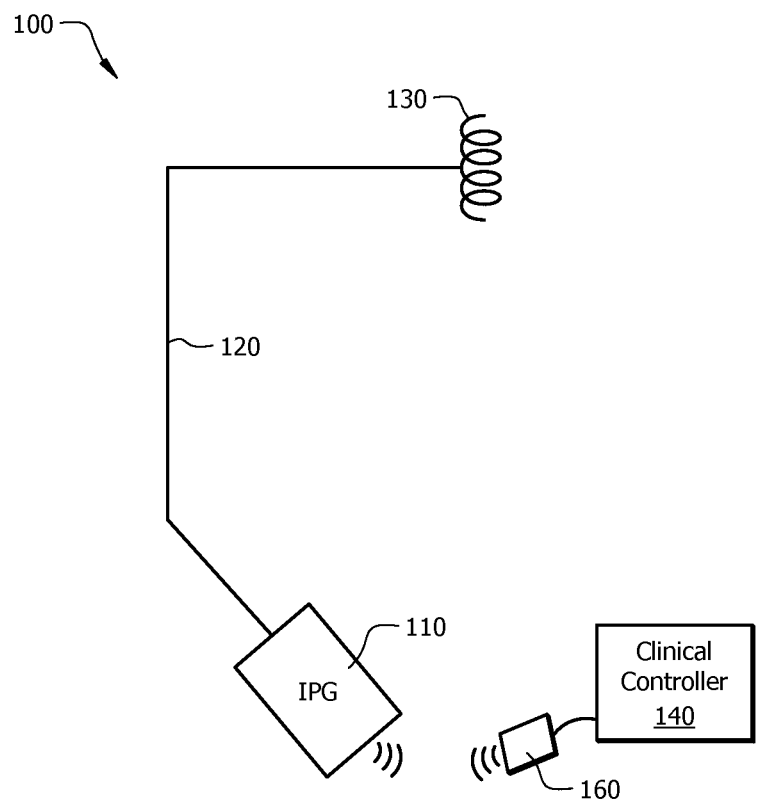
FIG. 6 depicts an implantable vagus nerve stimulation system.

As shown in FIG. 6, an implant system 100 may include an electrode 130, typically a cuff electrode. The electrode 130 is connected by a lead 120 to an implantable pulse generator (IPG) 110. The electrode 130 provides the electrical stimulation pulse train in close proximity to the vagus nerve. The lead 120 conveys the electrical current to stimulate the vagus nerve from the IPG 110 to the electrode 130. The IPG 110 includes internal software to receive commands from a clinical controller 140 as well as providing safety features. An example of a transcutaneous electrical stimulation system that could be adapted for use in the described therapy may be found in U.S. Pat. No. 7,797,042. Stimulation of the vagus nerve may be done at other sites along the vagus nerve and branches of the vagus nerve.

The clinical controller 140 is connected to the IPG 110 by radio frequency communication using a program interface 160. The Programming Interface (PI) 160 has a cable with a universal serial bus (USB) connector that plugs into the clinical controller 140 and converts the information from the clinical controller 140 into a radio frequency (RF) signal that is transmitted to the IPG 110. The PI 160 converts the digital signals from the computer and software into RF signals that can be transmitted through the air and skin to the device and receives RF signals back from the IPG 110. The IPG 110 then translates the signal and acts on the commands given it from the clinical controller 140. The PI 160 may have a cable of at least 6 feet long and may communicate with the IPG 110 at up to 2 meters from the PI 160. The PI 160 is powered via the USB connection and does not require any additional power source, such as battery, or additional power connection. Other communication methods could be implemented as appropriate.

Figure 7:
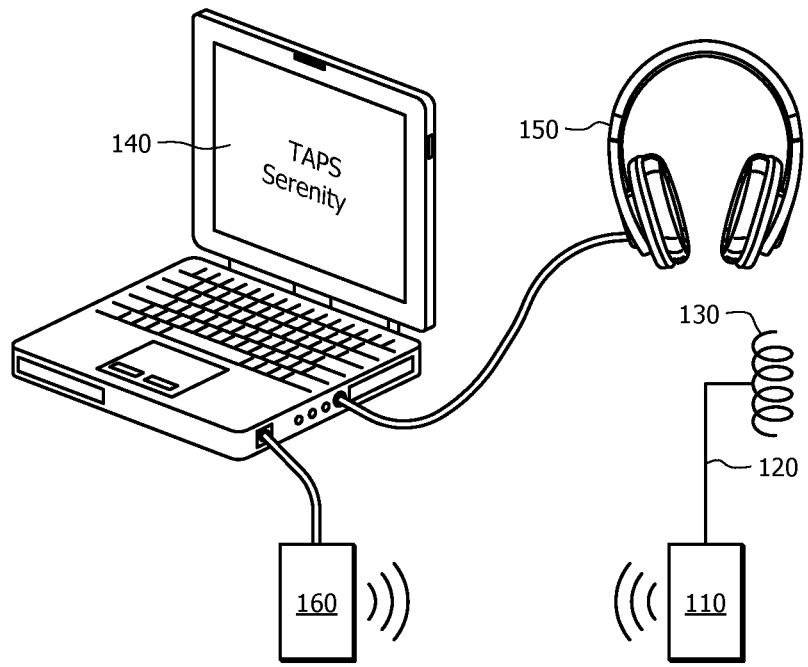
FIG. 7 depicts a paired VNS tinnitus therapy system.

As shown in FIG. 7, the external controller 140, or clinical controller, is typically a laptop computer running appropriate software. The clinical controller 140 is communicably connected to headphones 150 that are worn by the patient. Similar automated systems are described in U.S. Pat. Nos. 6,155,971 and 7,024,398, which are incorporated herein by reference.

Figure 8:
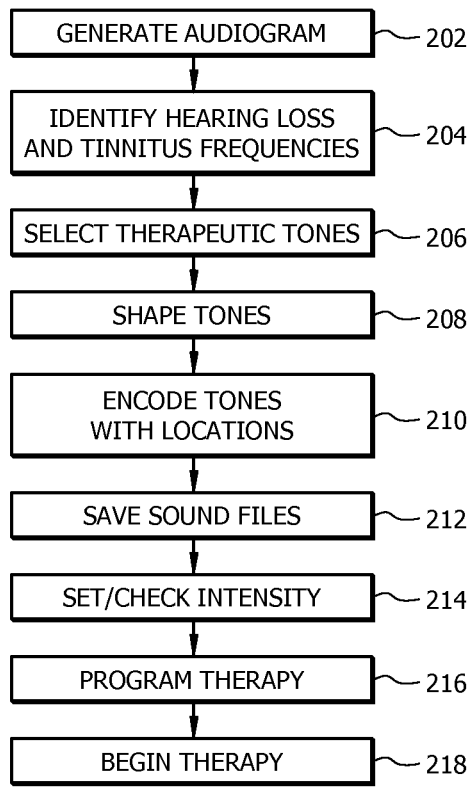
FIG. 8 is a flowchart depicting a patient therapy initiation routine.

FIG. 8 depicts a flow chart of the patient initialization and therapy process. An audiogram is generated by an audiologist at 202. The patient's hearing loss and tinnitus frequencies are identified at 204. Therapeutic tones are selected at 206. The tones are shaped at 208. The tones are encoded with locations at 210. The sound files are saved at 212. The intensity of each tone is set and checked at 214. The therapy parameters are programmed at 216. Therapy begins at 218.

Figures 9, 10:
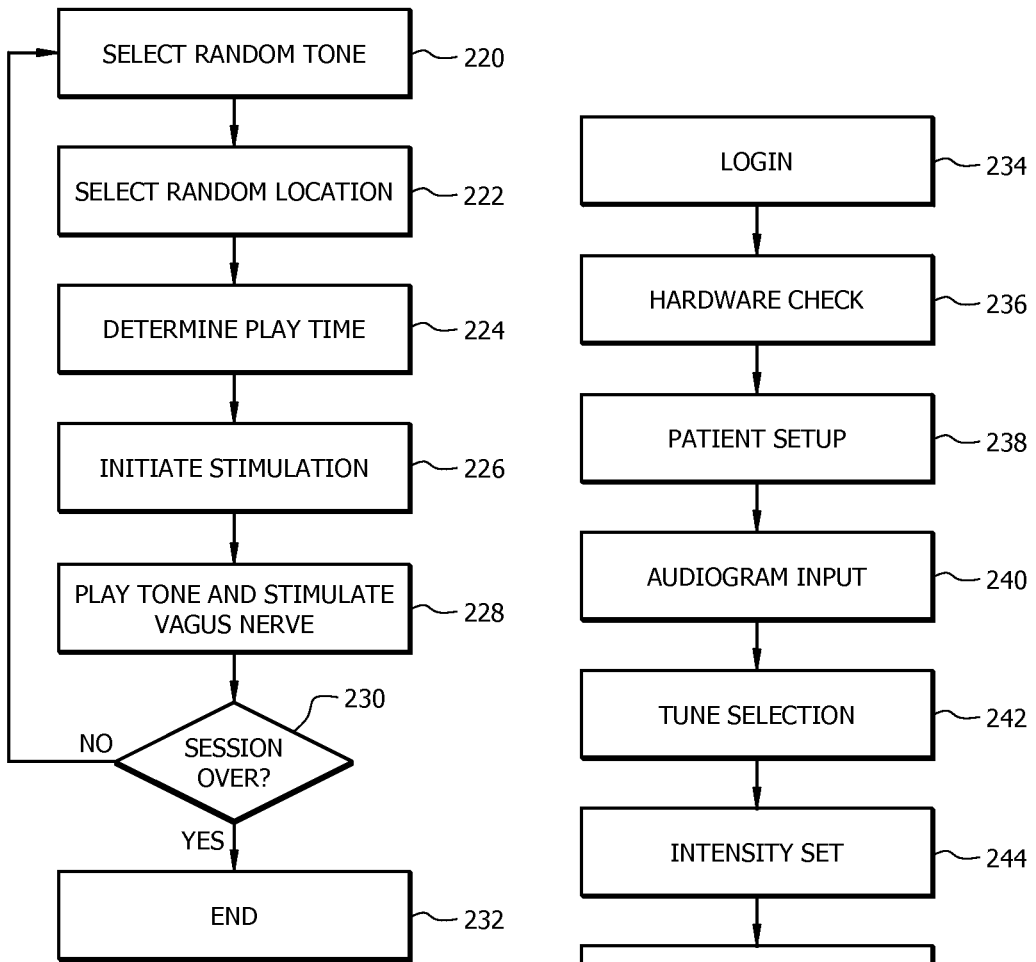
FIG. 9 is a flowchart depicting a tone selection routine.
FIG. 10 is a flowchart depicting a patient therapy routine.

When the therapy is delivered, a tone selection process as shown in FIG. 9 is used. A random tone is selected at 220. A random location is selected at 222. A playtime is determined at 224. The stimulation process is initiated at 226 so that the tone is played and the vagus nerve is stimulated at the same tine at 228. An end-therapy decision is made at 230. If the therapy continues, a new random tone is selected at 220. Otherwise, the therapy ends at 232.

The therapy is outlined in FIG. 10. The clinician logs into the software at 234. A hardware check is performed at 236. A patient set up is performed at 238. An audiogram is input at 240. Therapeutic tones are selected at 242. The intensity of the tones is set at 244. The stimulation parameters are set at 246. The session parameters are set at 248. The therapy is delivered at 250. The therapy data is saved at 252.

Figure 11:
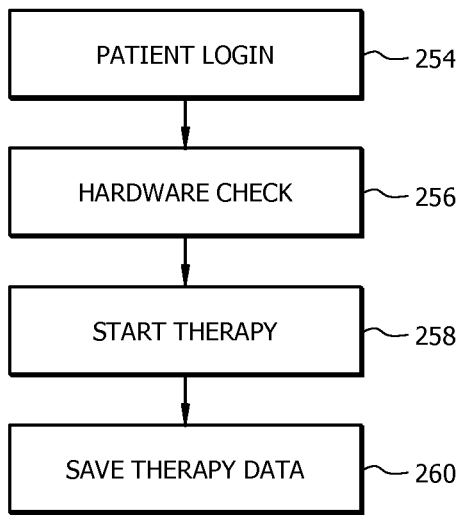
FIG. 11 is a flowchart depicting a patient home therapy routine.

A patient home therapy process is outlined in FIG. 11. A patient logs into the software at 254. A hardware check is performed at 256. The therapy begins at 258. The therapy data is saved at 260.

Figure 12:
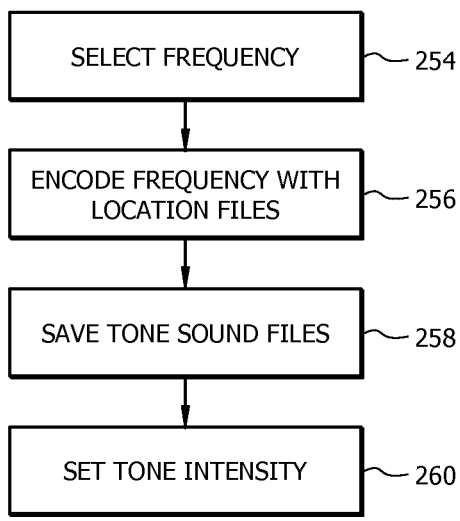
FIG. 12 is a flowchart depicting a sound file generation routine.

A tone preparation process is shown in FIG. 12. A therapeutic tone is selected at 254. Each tone is encoded with location files at 256. The tone sound files are saved at 258. The tone intensity is set at 260.

Specialized software has been developed to implement the tinnitus therapy. There are two modes in this software: At Home and Physician modes. The only mode available unless the Physician Login has been accessed and the appropriate password input is the At Home mode. In this mode only the Deliver Tinnitus Therapy option is enabled. The At Home mode allows patients to initiate a therapy session—this is the only function allowed by this mode. In order to access the rest of the program, the Physician Login button must be selected. This allows the Physician to type in a password which allows access to the rest of the software.

Figure 13:
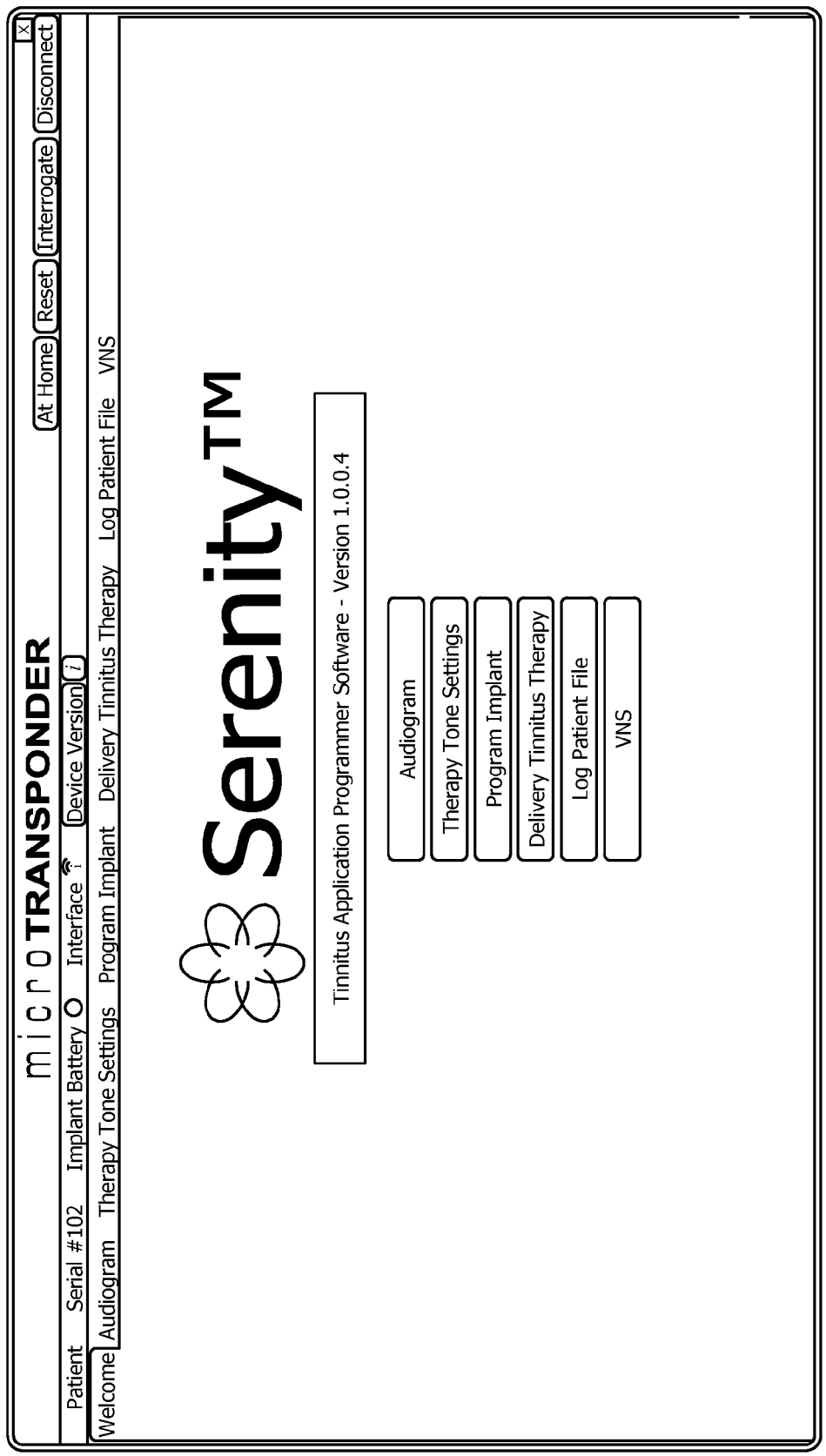
FIG. 13 is a screen shot of the paired VNS tinnitus therapy software menu.

To login and access all other TAPS screens, the audiologist or physician presses the Physician Login button (upper right menu bar, 4th button from the right—innermost button) and enters the password. This opens full access to the software and allows all settings to be established and modified. At this point the program is "unlocked" and all menus in the program are available, as shown in FIG. 13. The first option, Audiogram, is used by the physician/audiologist to enter the audiogram data. The second option, Therapy Tones Settings, is used by the physician/audiologist to set the tones. The third option, Program Implant, is used to set the stimulation settings and allows impedance checks. The fourth option, Deliver Tinnitus Therapy, is used only during clinical trials. It allows the physician or audiologist to set a sham-control group that does not receive paired VNS, but instead receives tones-only or VNS-only (in sequences such that the patient receives tones and VNS, but they are not received simultaneously). This allows blinding to be maintained in a parallel study design. The "Log Patient File" option allows a patient's file to be saved. The "VNS" option allows independent delivery of VNS.

In order for therapy to be delivered, the tones and stimulation must be set by the audiologist, physician, or healthcare worker. The tones must be set first. To set the tones, the Audiogram and the Therapy Tone Settings tabs must be completed. The Audiogram is accessed as shown in FIGS. 14-22.

Figure 14:
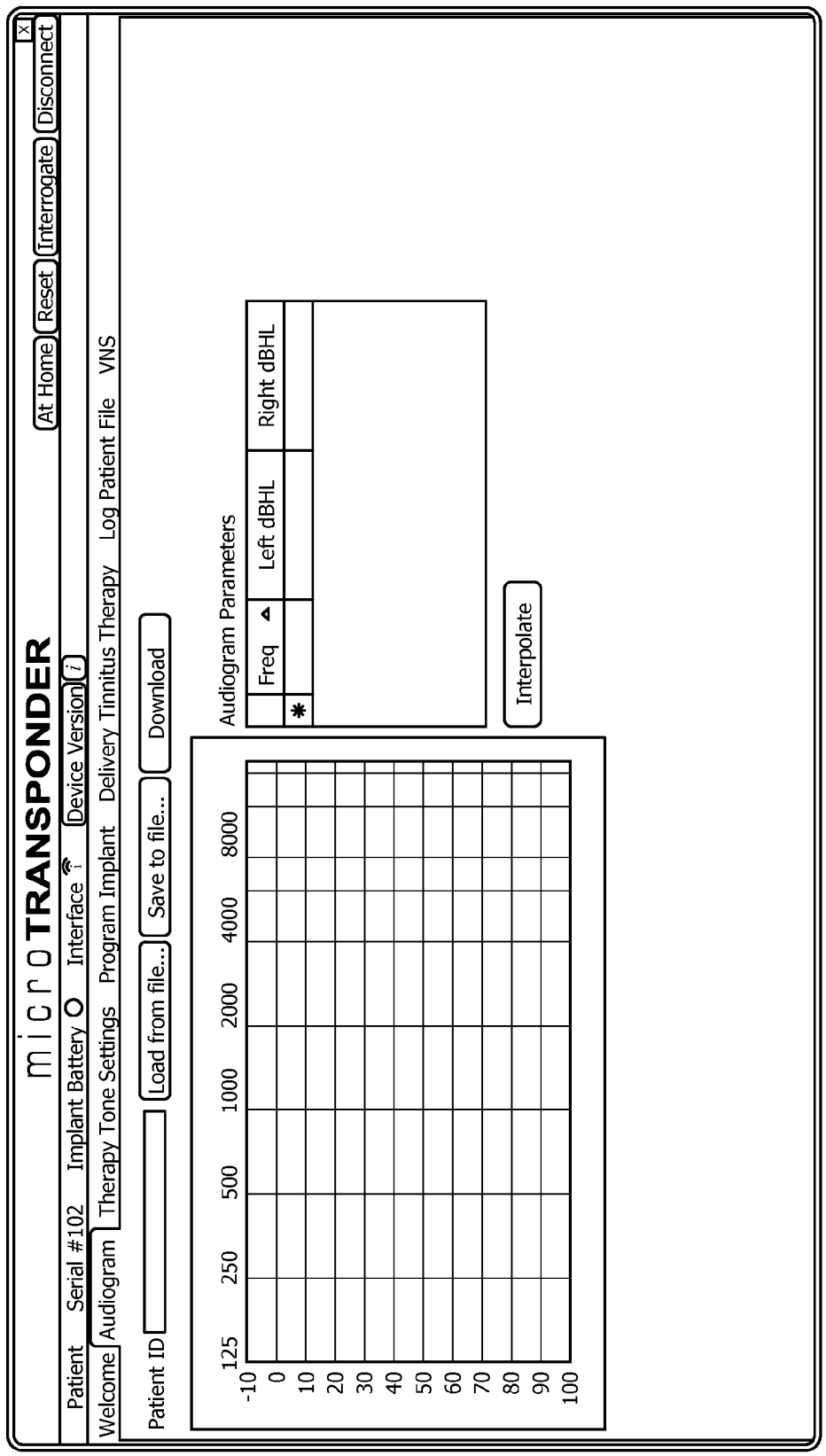
FIG. 14 is a screen shot of an audiogram input screen.
Figure 15:
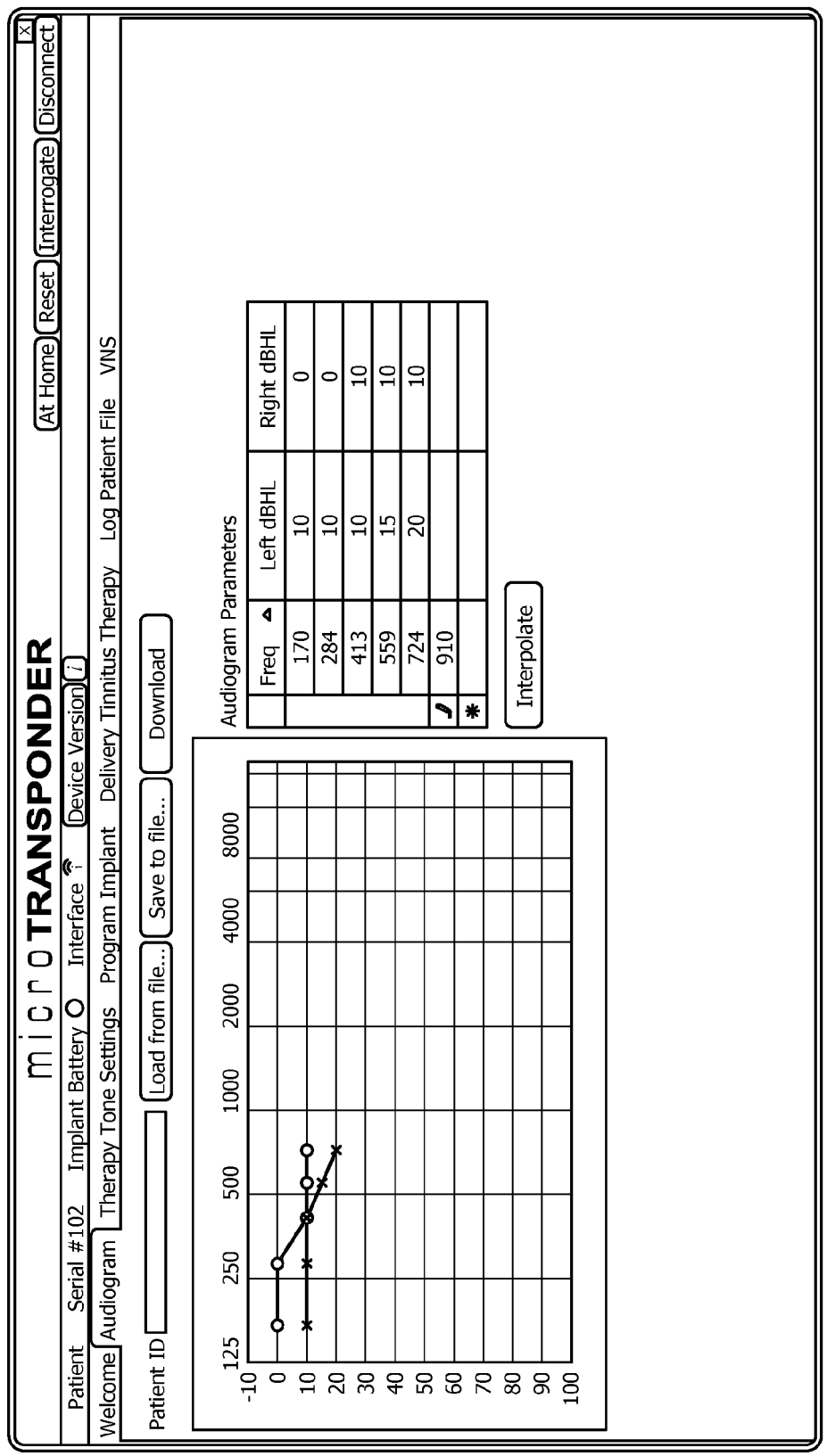
FIG. 15 is a screen shot of an audiogram input screen with sample data input.
Figure 16:
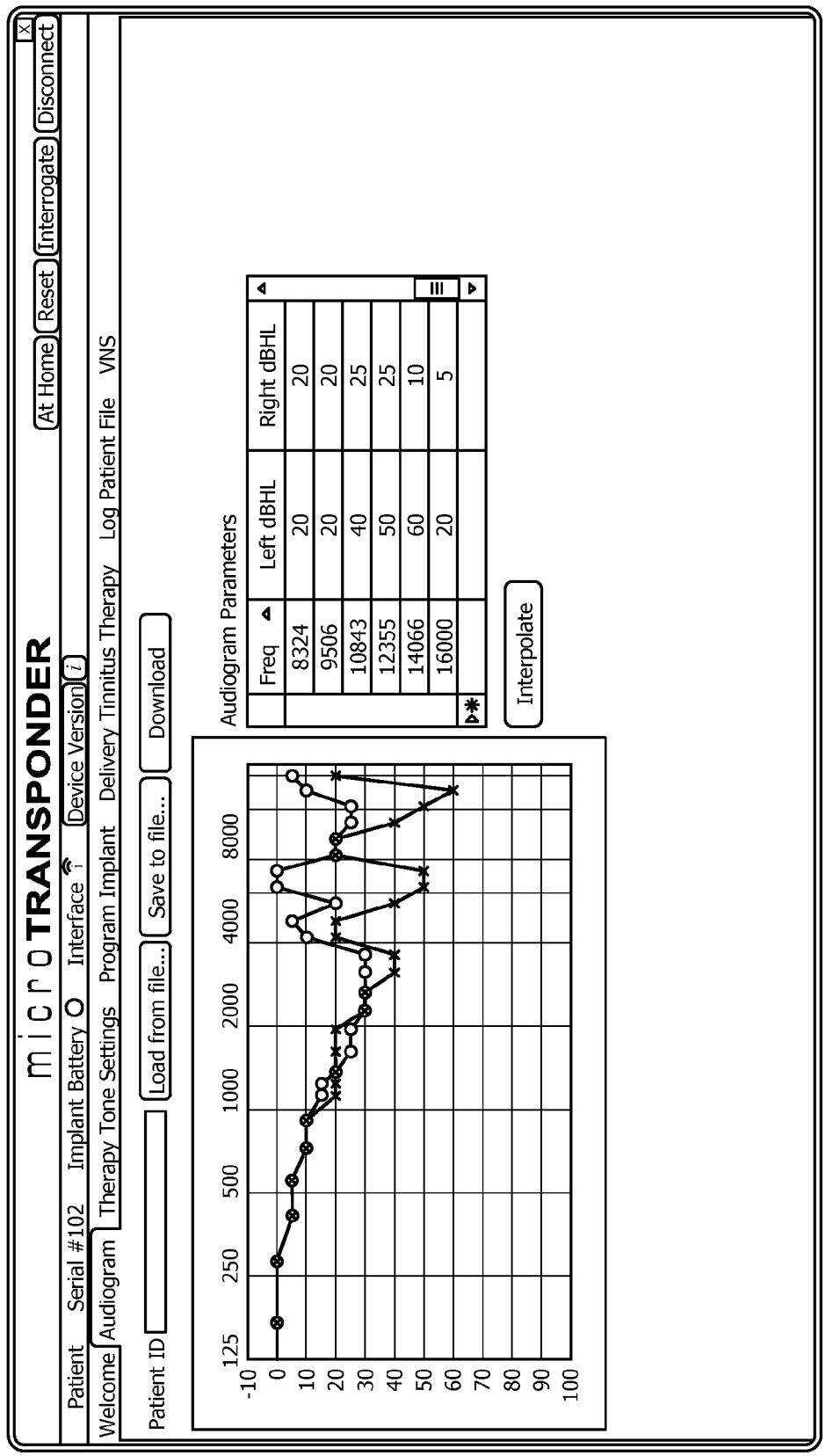
FIG. 16 is a screen shot of interpolated audiogram data.

FIG. 14 is the screen where Audiogram information is added and interpolated. The information may be loaded from a file that was previously generated in by the specialized software or entered manually. Once the audiogram is entered, it can be saved to a file. In order to manually enter the data, the audiologist or physician clicks in the appropriate cells of the Audiogram Parameters table and types the values in as needed for frequency and hearing loss of both the Left and Right ears, as shown in FIG. 15. The user must interpolate the audiogram in order to be able to access Therapy Tone Settings and continue with therapy set up. In order to interpolate the data into the Therapy Tone Settings, following the successful entry of all audiogram parameters, the Interpolate button must be selected, as shown in FIG. 16. The interpolated data populates the Therapy Tone Parameters table on the Therapy Tone Settings automatically. This data will not be saved until either the Save to file . . . button or the Download button is selected. The Save to file . . . function prompts the user to save the file in a preferred location (an external USB drive is recommended), and the Download function saves the data into the IPG. In order to deliver proper therapy, the Download function must be performed so that the therapy information is loaded into the IPG's memory.

Figure 17:
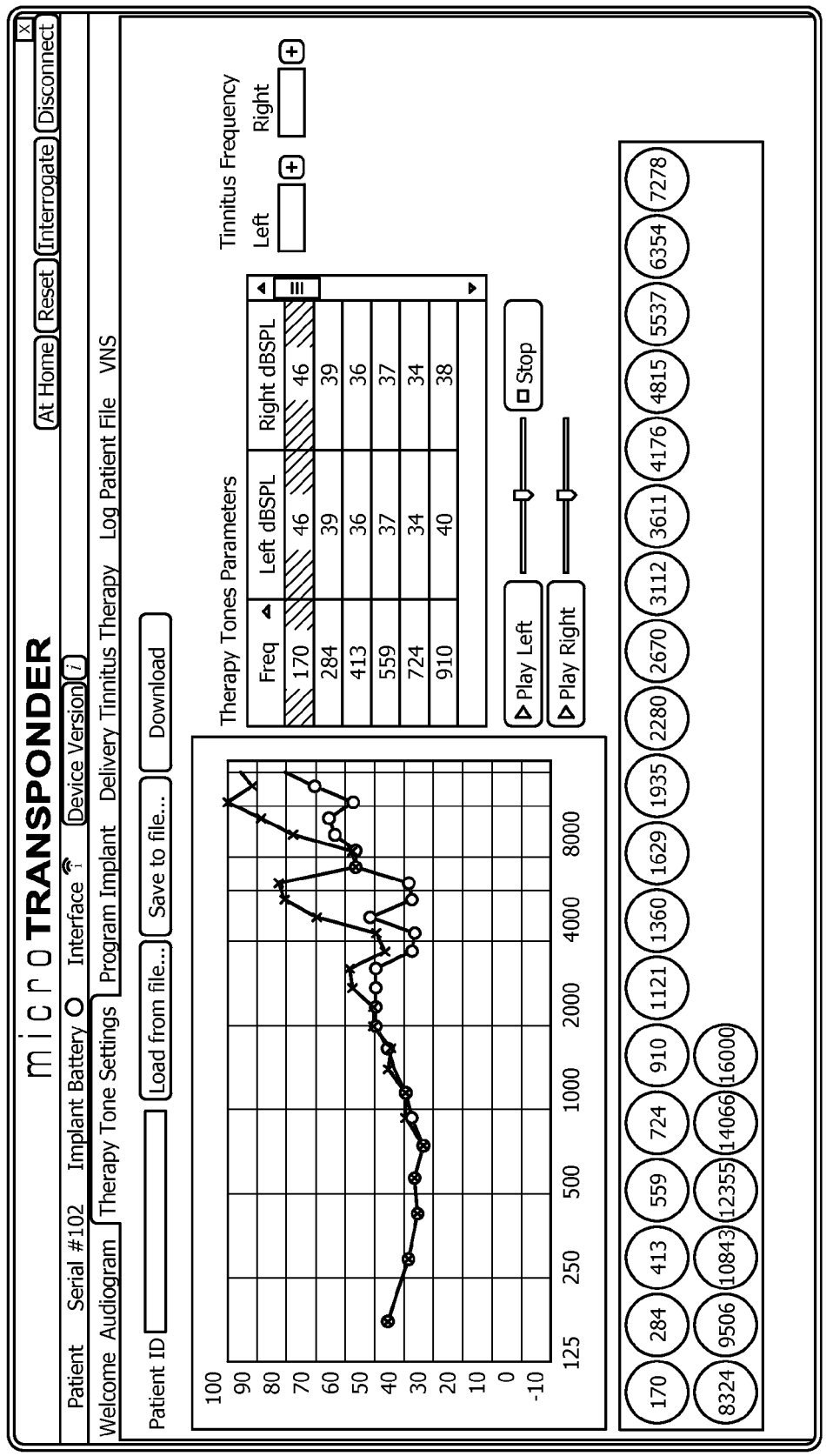
FIG. 17 is a screen shot of therapeutic tone selection.

As shown in FIG. 17, after the Audiogram parameters are populated with Audiogram-based data (either manually or from a file) and subsequently interpolated, the "Therapy Tone Settings" button can be selected. The Tinnitus Frequencies can now be added. This is also where the manual testing of the tones occurs and can be adjusted. Frequencies can be deselected in order to notch out frequencies around the Tinnitus frequency or frequencies.

Figure 18:
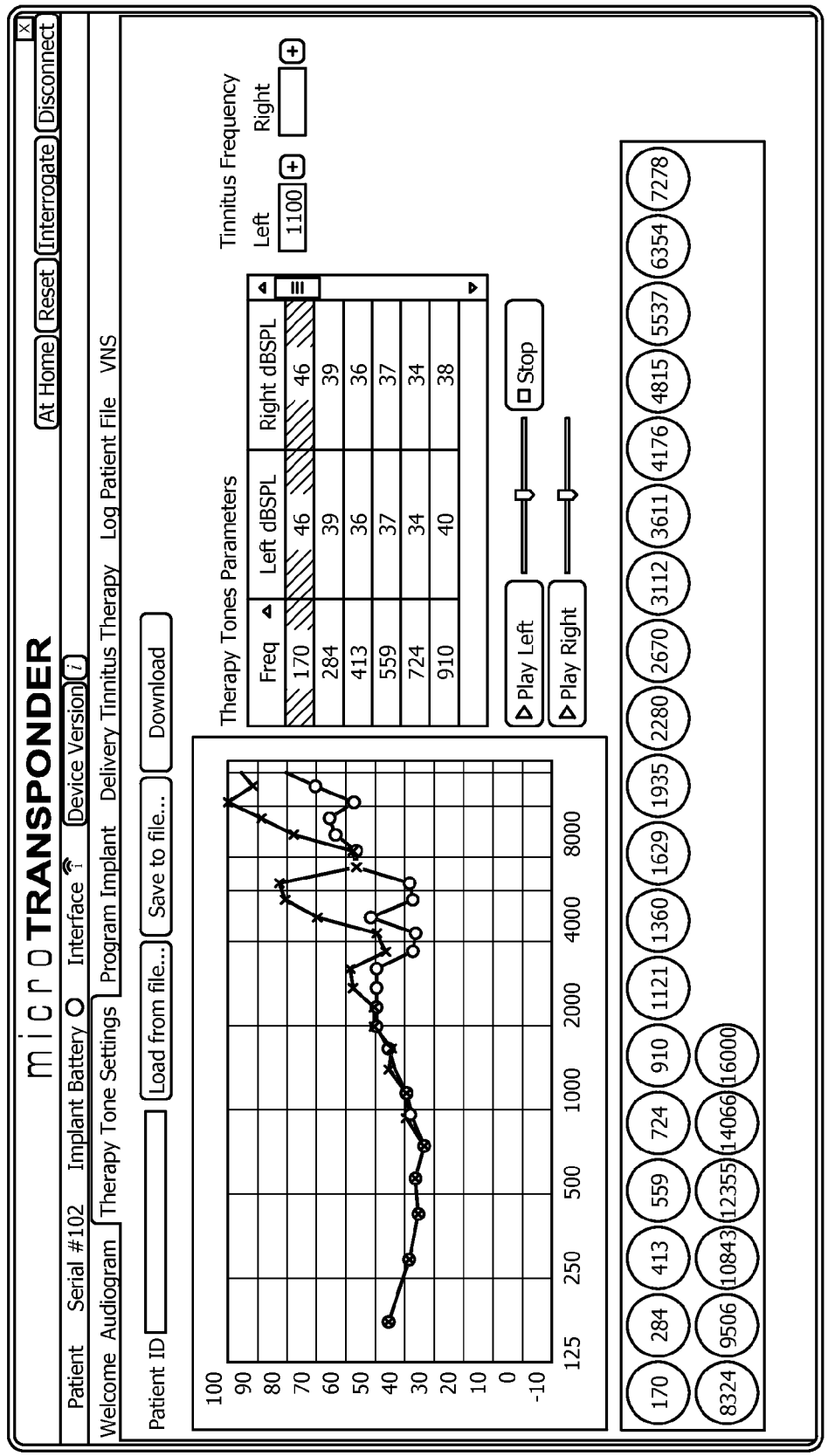
FIG. 18 is a screen shot of therapeutic tone selection with a tinnitus frequency notch.

For example, as shown in FIG. 18, if a patient has tinnitus in the left ear, around a frequency of 1,100 Hz, the audiologist is recommended to notch out tones being played in a ½ Octave around 1,100 Hz. To do this, the frequency of 1,100 is input into the drop down menu under Left and Tinnitus Frequency as shown below (right middle of screen, FIG. 18). The software will then automatically select the frequencies of 910, 1121, and 1360 Hz. If necessary, the audiologist or physician can manually modify this by clicking on a frequency and selecting or deselecting the frequency.

Figure 19:
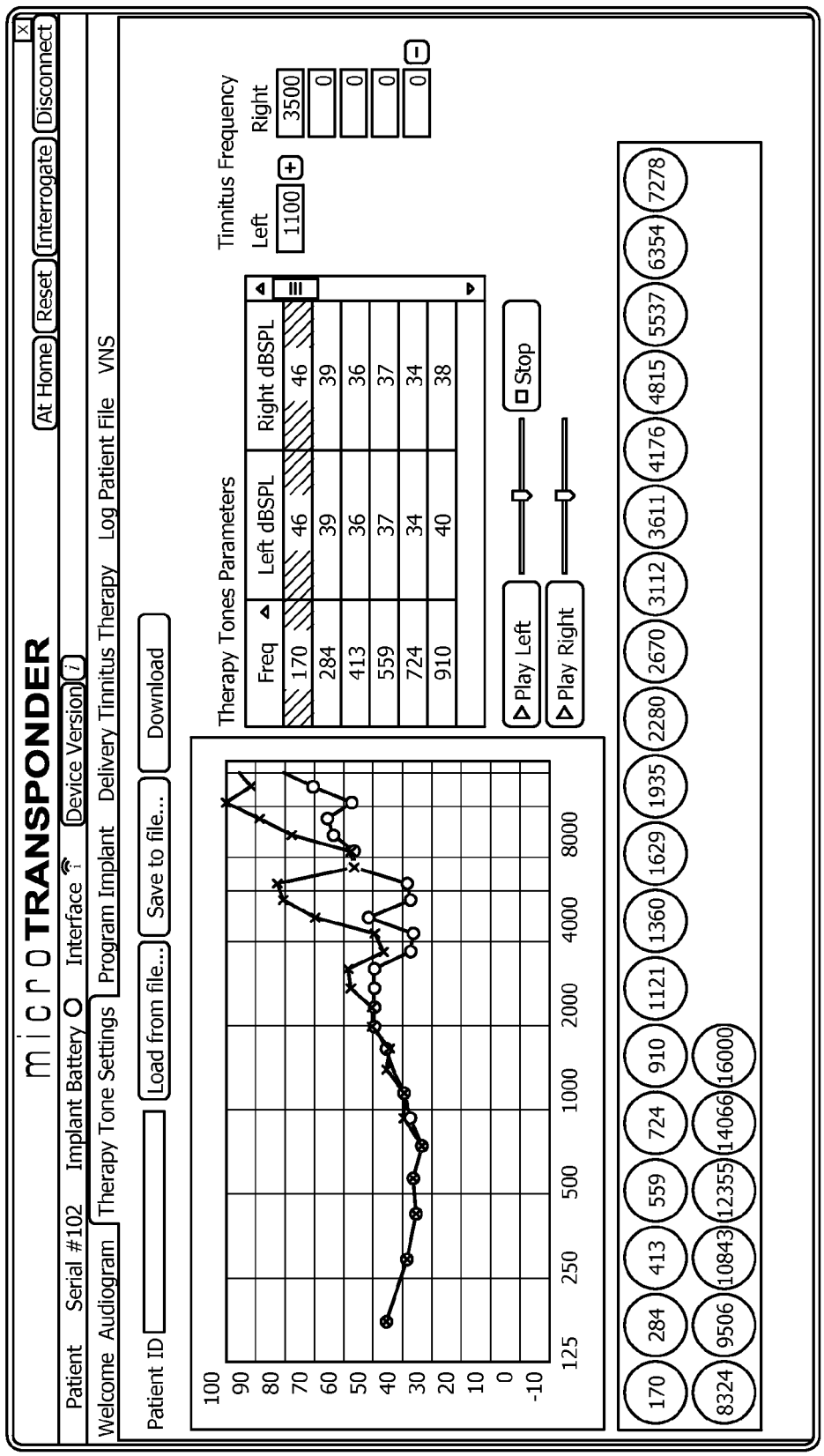
FIG. 19 is a screen shot of therapeutic tone selection with multiple tinnitus frequency notches.

As shown in FIG. 19, if the patient also has a tinnitus frequency of 3500 in the right ear, the audiologist would add "3500" in the Right—Tinnitus Frequency box, and the software will again automatically "notch out" frequencies ½ octave around 3,500 Hz. Note that the +box next to the tinnitus frequency can be clicked, and additional tinnitus frequencies can be added.

Figure 20:
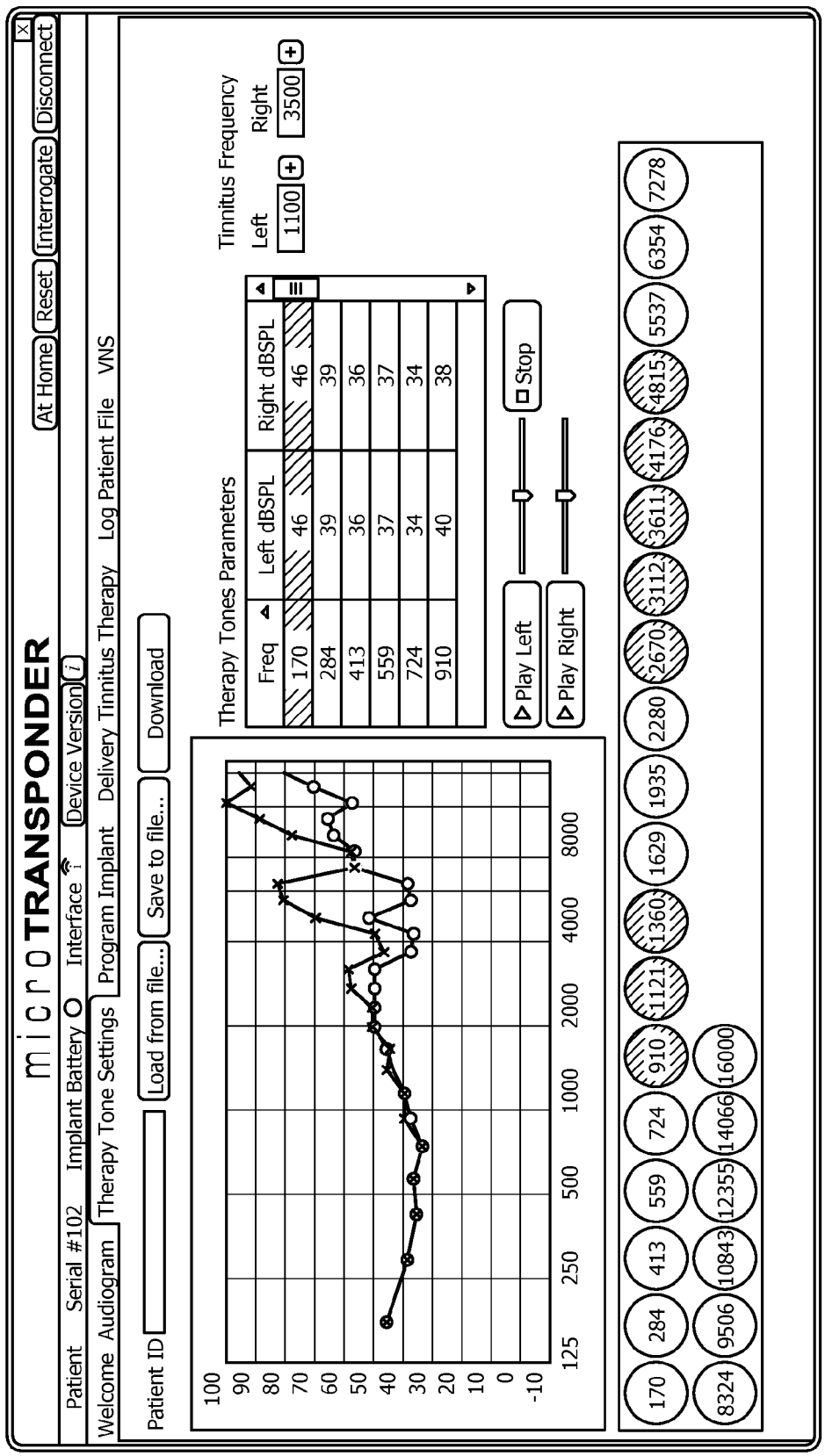
FIG. 20 is a screen shot of therapeutic tone selection with two tinnitus frequency notches.

As shown in FIG. 20, two tinnitus frequencies (1,100 Hz and 3,500 Hz) are shown, and any frequency within a ½ octave of those frequencies are notched out (inactive frequency buttons are grayed), so that the tinnitus frequencies cannot be selected.

Figure 21:
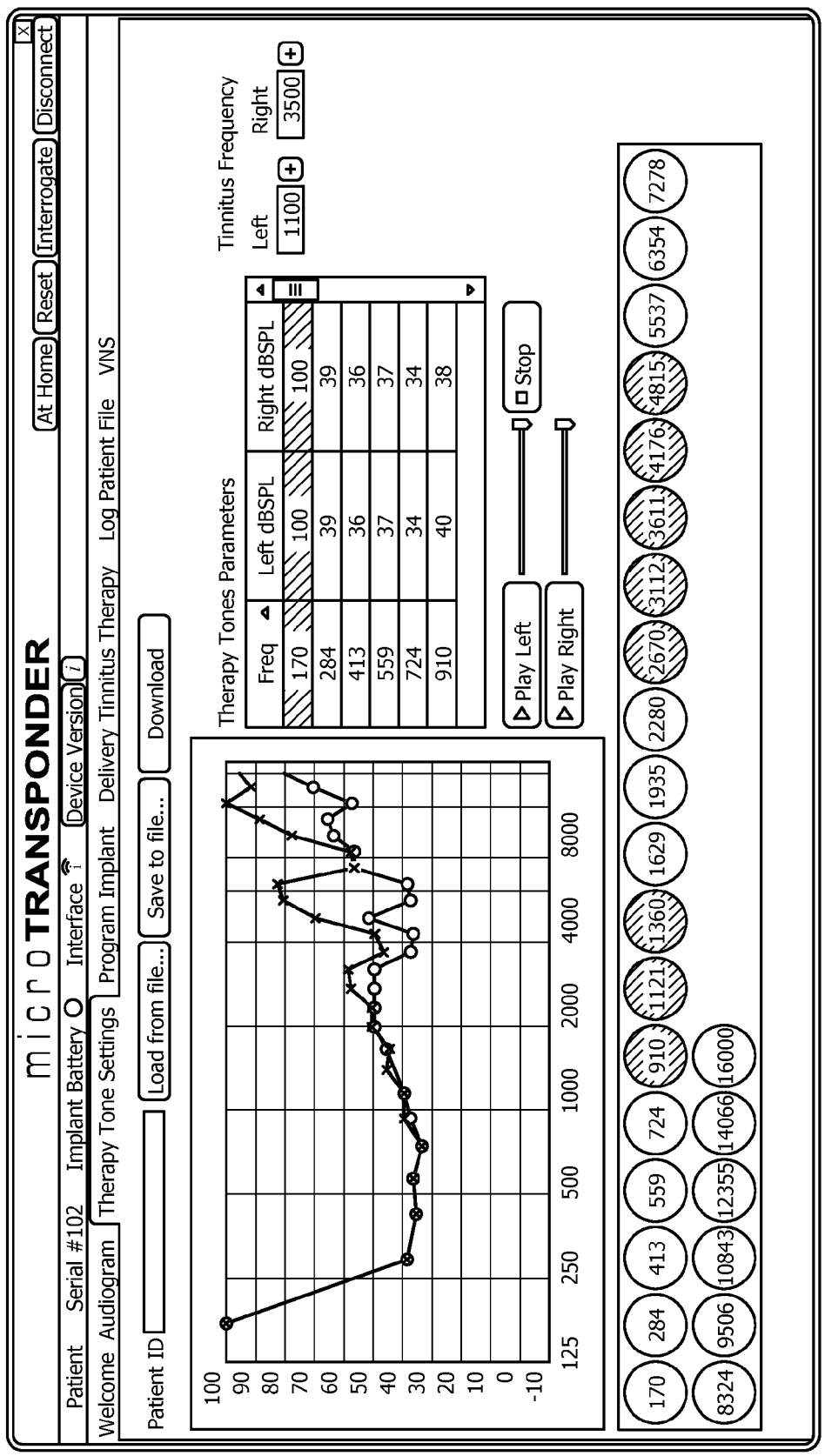
FIG. 21 is a screen shot of therapeutic tone volume setting.

As shown in FIG. 21, the tone volume for the sound level that each tone is played at for each frequency is also available for input. The volume played in the left and right ear is adjustable—in the example below, it is 170 Hz. Frequency is being adjusted to 100 dB for both the left and right ears. The Play Left or Play Right button can be selected to test the tones and volume levels.

Figure 22:
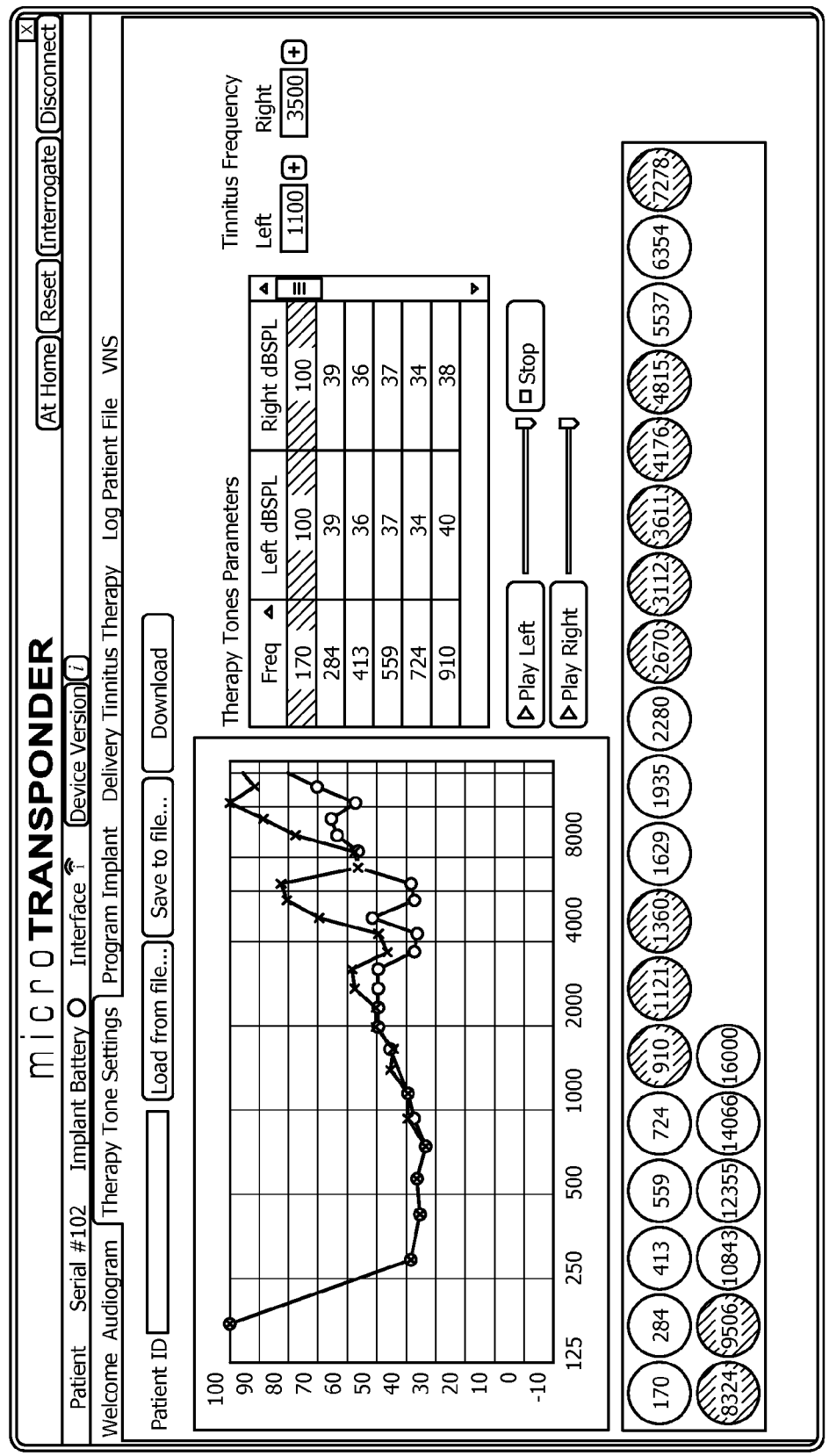
FIG. 22 is a screen shot of therapeutic tone selection with additional notches.

FIG. 22 shows an additional three frequencies being notched-out (7278, 8324, and 9506 Hz), as indicated by the gray deselected buttons near the bottom of the screen.

Figure 23:
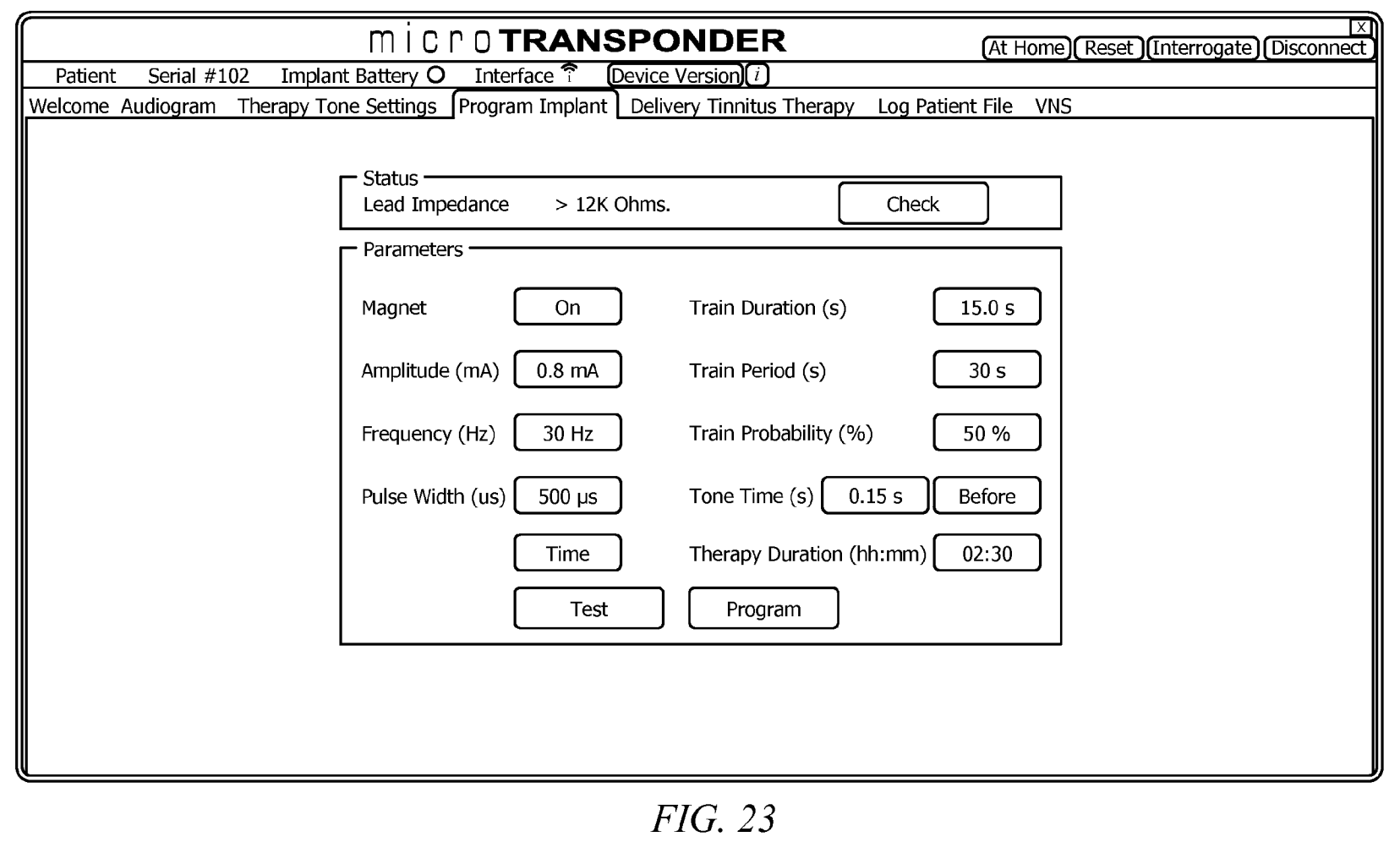

The Program Implant menu, as shown in FIG. 23, allows the user to set the VNS Parameters, check the lead impedance, and then test and ultimately program the parameters into the IPG. For each of the settings (Magnet, Train Duration, Amplitude, Train Period, Frequency, Train Probability, Pulse Width, Tone Time and Therapy Duration), the box next to the setting is clicked, and all available parameters are shown in a drop down box. The appropriate value is selected for each parameter. After all of the parameters are set, the user may Test or Program the displayed parameters. It is recommended the user verify that the VNS settings chosen are tolerable for the patient. Selecting the Test button delivers a single train of stimulation per the parameters displayed in the Parameters menu for this purpose. This does not permanently program the IPG, but only performs a one-time stimulation.

Once the user is satisfied that the chosen parameters are appropriate and tolerable, the Program button must be selected in order to program the IPG with the therapy parameters displayed in the Parameters menu. The values programmed via the Program function are input into the IPG and all subsequent therapy sessions will be performed at these parameters. The user can modify the parameters at any time by selecting new parameters and programming them into the IPG. The user may also want to verify the lead impedance. In the Status portion of the Program Implant menu the lead impedance can be checked by selecting a Check button. Doing so delivers a small current pulse through the lead to calculate the lead impedance. The user shall ensure that the lead impedance check does not cause discomfort in the patient. After the check button is selected, the lead impedance value is shown. For any value above 10,000 ohms, a Warning screen above reminds the patient to contact their physician or audiologist to see if any action needs to be taken.

Figure 24:
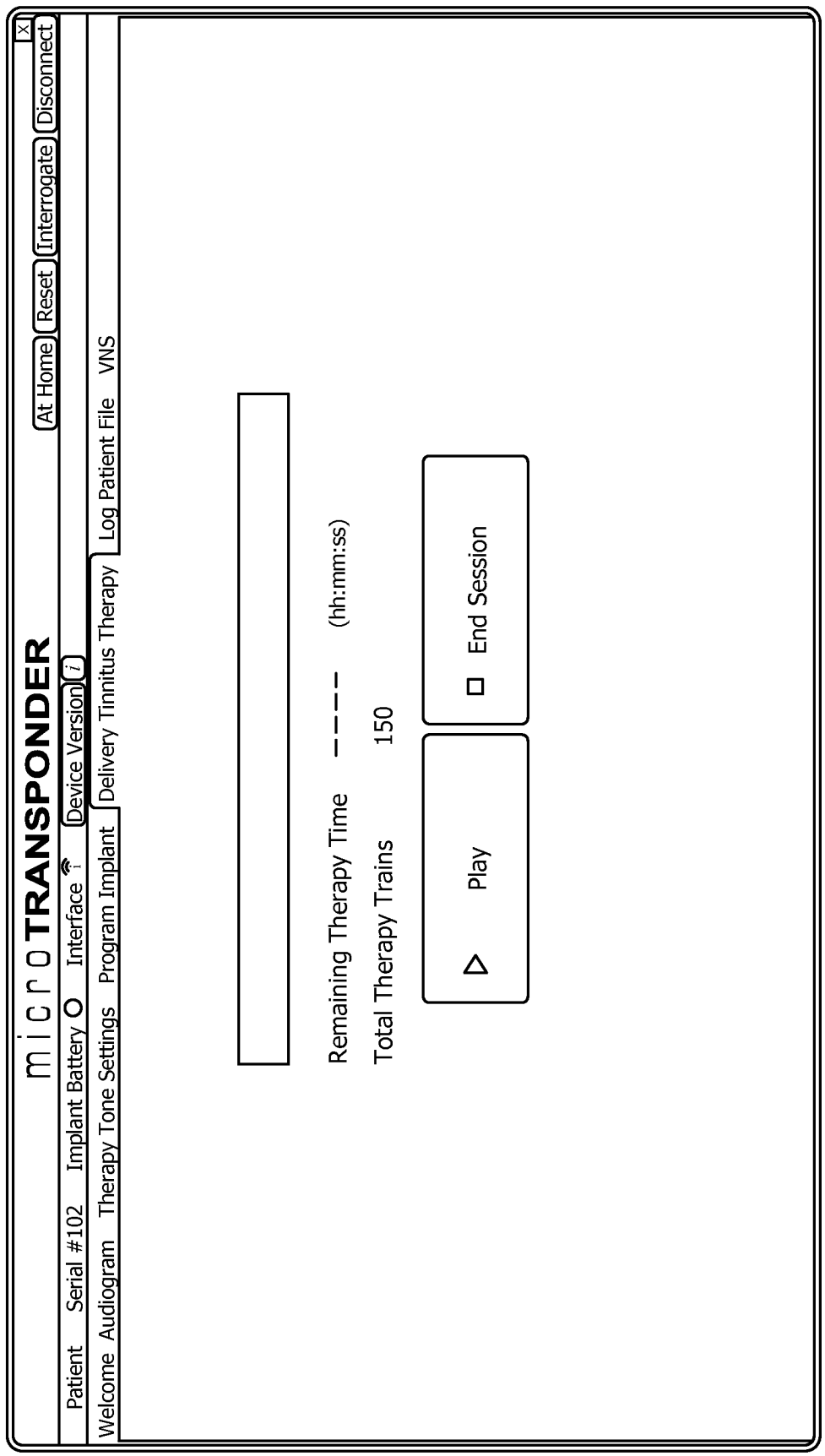
FIG. 24 is a screen shot of therapy delivery.

As shown in FIG. 24, the therapy is delivered by selecting the PLAY button. For home therapy, the patient may be given limited access to some features in the specialized software. The patient can administer therapy to themselves, and all the data corresponding to the session will be recorded for subsequent review by the clinician. Headphones have been selected to deliver consistent tone intensity across the full range of frequencies. Clinical and pre-clinical data has been collected to support the effectiveness of the formatting.

The peripheral nervous system, central nervous system including the brain and spinal cord can all be used as stimulation locations. The choice of stimulation location largely determines the behavioral and neurophysiologic outcome. Even though similar neural populations are activated by input from two different locations, the manner in which they are activated, for example, the pattern of activity generated within the neuron population will depend on the time course of activation, release of one or more neuromodulators, attention state, etc.

The neurophysiological consequences therefore are bound to be different. Given the large (and unknown) number of variables that can influence the activation of a given neural population, the mechanisms are likely to be complex and unpredictable. There is no calculus to determine which locations will produce which effects. Finding a location that produces a given effect can only be done experimentally. It is not valid to suggest that stimulation at one location makes it obvious to stimulate at a different location, even if the goal is to stimulate the same population of neurons.

The same can be said for stimulation parameters. At a given stimulation location, stimulation according to one set of parameters will not necessarily produce the same (or similar) effects as a stimulation according to another set of parameters. The frequency of stimulation, the current amplitude of stimulation, the duration of each stimulation, the waveform of stimulation, as well as other stimulation parameters can change the results of stimulation.

Our experiments have shown that the effect generated by VNS pairing is very short, less than 15 seconds. A first tone at a first frequency when paired with VNS generated an increase in the number of neurons that respond to the paired frequency. A second unpaired tone at a second frequency, played 15 seconds after the paired VNS did not show a corresponding increase in the number of neurons that respond to the second frequency. Nothing in the prior art indicates this kind of precise timing requirement.

Similarly, we have performed experiments in which multiple tones at a given frequency were paired with VNS and given 30 seconds apart. This was done in the tinnitus study (Engineer et al., 2011) in which VNS was paired with each of the randomly interleaved tones every 30 seconds (e.g., 1.3 kHz+VNS, then wait for 30 seconds, then give 6.3 kHz+VNS, then wait for 30 seconds, and so on). The tones were selected such that they surrounded the tinnitus frequency and the tinnitus frequency itself was excluded. The idea was to shrink the representation of the tinnitus frequency thereby restoring the map and synchronous activity back to normal. When the same tones were presented 8 seconds apart, the effect was less than if the tones were presented 30 seconds apart, which was surprising.

To cite another example, we have performed a series of experiments where a tone is repeatedly paired with a foot-shock to establish a conditioned fear response. Subsequently, when the tone was presented without a foot-shock, the rat would freeze, anticipating a foot shock. If the tone, without the foot-shock, is then presented repeatedly, the fear caused by the tone would eventually be extinguished, undoing the conditioning. By pairing the tone (without the foot-shock) with VNS, the fear is extinguished much more quickly. However, presenting the tone by itself and then giving VNS minutes later, the fear is extinguished at the normal rate. These results demonstrate that the precise timing between VNS and the event, as well as the interval separating the VNS-event pairings appear, to be important for inducing highly specific plasticity."

Neurostimulation does not behave in a predictable fashion. Different stimulation locations produce different results, even when both locations are cranial nerves. For example, synchronization in the cerebral cortex is a manifestation of epilepsy. Stimulating the vagus nerve causes desynchronization of the cortex neurons, which has been proposed as a potential mechanism for how vagus stimulation prevents an epileptic seizure. Stimulation of the trigeminal nerve, another cranial nerve, causes desynchronization as well. To determine whether the plasticity induced by VNS is specific to the vagus nerve, we paired stimulation of the trigeminal nerve with a 19 kHz tone. However, when we paired trigeminal stimulation with a tone, in the same way we paired VNS with a tone, we did not observe any plasticity that was specific to the paired tone. Pairing the trigeminal stimulation with a tone at a given frequency did not change the response to that frequency even though it caused desynchronization as in the previous study. Each stimulation location is unique across the full range of effects. It appears that VNS may be uniquely suited to direct cortical plasticity and suggests that the vagus nerve is likely a key conduit by which the autonomic nervous system informs the central nervous system of important stimuli.

The VNS pairing therapy is more than the sum of its constituent parts. Simply playing a tone at a given frequency, without VNS, does not result in a change in response to the frequency. Similarly, VNS by itself did not produce any changes in response to any frequency. Only by precisely pairing VNS with a tone at a given frequency induces a change in response to the frequency.

Both VNS pairing and nucleus basalis stimulation (NBS) pairing have been shown to change the number of neurons responding to a paired frequency. To be effective, the current amplitude parameter of the stimulation for VNS pairing is more than twice the current amplitude used for NBS pairing. There is an important difference between the neuromodulators released by NBS from those released by VNS, so significant differences between the results of NBS and VNS are expected.

Another experiment demonstrated that pairing a single tone at a specified frequency with VNS increased the number of neurons responding not only to that frequency but to close frequencies, e.g., increased the bandwidth compared to control rats. For NBS pairing, the bandwidth was not significantly different from control rats. Unlike VNS pairing, NBS pairing is highly invasive and may be unsuitable to provide a practical therapeutic benefit. Similar results in one circumstance cannot be extended to predict similar results in another, even slightly different, circumstance. Different stimulation parameters have to be used for effective VNS pairing and NBS pairing.

We observed that 30 seconds of VNS at 30 Hz and 0.8 milliamps (mA) transiently decreased the blood oxygen saturation level ($SpO_2$) in 3 rats. The standard 0.5 second VNS used in this study had no measurable effect on either heart rate or oxygen saturation (data not shown). These results are consistent with visual observations that brief VNS causes no noticeable behavioral response. For example, rats did not stop grooming or awaken when brief VNS was delivered.

Our observations that brief VNS (1) caused no behavioral response, (2) caused no change in heart rate, and (3) caused no change in blood oxygen saturation, suggest that VNS induced plasticity is not equivalent to pairing tones with a painful or irritating stimulus (as in footshock or air puff).

Three weeks after the end of therapy, neural recordings were obtained from 13 of the 18 noise exposed rats. We continued to follow 4 rats (2 therapy and 2 sham rats) for an additional two months. Consistent with previous reports, the untreated rats continued to exhibit impaired gap detection 3.5 months after the noise exposure. Signs of impairment of gap detection did not return in either of the rats that received the VNS-multiple tone therapy. These results confirm that the VNS-multiple tone therapy causes a long lasting reversal of noise induced perceptual hearing abnormalities in rats.

In an effort to document changes in cortical synchronization in unanesthetized rats, we looked for systematic effects of VNS-multiple tone pairing on Electroencephalography (EEG) in noise exposed rats (7 VNS paired and 4 VNS alone rats). Although the data is variable because the animal's behavioral state was uncontrolled and the EEG electrode was located at the vertex and not over auditory cortex, we nevertheless observed statistically more gamma power relative to alpha in treated rats compared to untreated rats during the last week of therapy ($p<0.05$), but no difference between the EEG of therapy and VNS alone rats during the first week. These results are consistent with animal studies that tinnitus can be associated with abnormal cortical synchronization and clinical reports of reduced alpha and increased gamma in tinnitus patients. As in our anesthetized recordings, the degree of EEG change was not significantly correlated with gap impairment in individual rats.

The pairing as it relates to tinnitus is notably unique. We are not pairing just random sounds. We are not doing some kind of auditory training or improving perception of one sound over another. The key is that we are deliberately pairing the non-tinnitus frequency. The reason is that pairing the non-tinnitus frequency results in a decrease in the area of the brain responding to the tinnitus frequency and decrease the synchronous firing of neurons. By reducing the response to the tinnitus frequency and decreasing synchrony, we are able to reduce tinnitus symptoms. No one has before shown that the symptoms of tinnitus can be improved by excluding specific sounds and including specific sounds. A drug cannot work selectively in this way, nor can cortical stimulation. VNS has the specificity to do this.

None of the description in the present application should be read as implying that any particular element, step, or function is an essential element that must be included in the claim scope: the scope of patented subject matter is defined only by the allowed claims. Moreover, none of these claims is intended to invoke paragraph six of 35 USC section 112 unless the exact words "means for" are followed by a participle. The claims as filed are intended to be as comprehensive as possible, and no subject matter is intentionally relinquished, dedicated, or abandoned.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 5, 4, etc.; greater than 0.10 includes 0.11, 0.12, 0.15, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 5 percent, 4 percent, 5 percent, . . . , 50 percent, 51 percent, 52 percent, . . . , 75 percent, 76 percent, 77 percent, 78 percent, 77 percent, or 100 percent. Moreover, any numerical range defined by two R numbers as defined in the above is also specifically disclosed. The use of the term "about" means±10 percent of the subsequent number unless otherwise defined. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A system for treating tinnitus comprising:
a clinical controller executing tinnitus therapy software;
a vagus nerve stimulation (VNS) implantable pulse generator (IPG) in communication with the clinical controller and receiving stimulation signals from the clinical controller;
a VNS lead connected to the VNS IPG;
a VNS electrode connected to the VNS lead and receiving stimulation signals through the VNS lead from the VNS IPG; and
a sound generator connected to the clinical controller, wherein the clinical controller plays selected sound files through the sound generator while sending stimulation signals to the VNS IPG such that respective selected sounds of respective selected sound files may be heard by a patient while a stimulation pulse train at the VNS electrode causes the patient's vagus nerve to be stimulated, wherein
the system is configured to receive input based on the patient's tinnitus frequency, and
the selected sounds are therapeutic tones, and the system is configured to automatically play the therapeutic tones such that they are at least a half-octave above the patient's tinnitus frequency.

2. The system of claim 1, wherein the clinical controller is a laptop computer.

3. The system of claim 1, wherein the VNS IPG receives stimulation parameters from the clinical controller.

4. The system of claim 1, wherein the selected sounds are therapeutic tones, and wherein the system is configured to execute a session that automatically applies at least 100 therapeutic tones per day.

5. The system of claim 1, wherein the selected sounds are therapeutic tones, and wherein the system is configured to execute a session that automatically applies at least 300 therapeutic tones per day.

6. The system of claim 1, wherein the selected sounds are therapeutic tones, and wherein the system is configured to play each therapeutic tone such that each therapeutic tone has a duration of about 500 milliseconds.

7. The system of claim 1, wherein the selected sounds are therapeutic tones, and wherein the system is configured to execute a session that repetitively plays each of the plurality of therapeutic tones in a temporally random manner.

8. The system of claim 1, wherein the selected sounds are therapeutic tones, and wherein the system is configured to execute a session that repetitively plays each of the plurality of therapeutic tones in a frequency-based random manner.

9. The system of claim 1, wherein the selected sounds are therapeutic tones, and wherein the system is configured to execute a session that plays each therapeutic tone such that it is a pure tone.

10. The system of claim 1, wherein the selected sounds are therapeutic tones, and wherein the system is configured to shape the therapeutic tones with a ramp function.

11. The system of claim 1, wherein the selected sounds are therapeutic tones, and wherein the system is configured to encode the therapeutic tones with location data.

12. The system of claim 1, wherein the selected sounds are therapeutic tones, and wherein the system is configured to automatically play the therapeutic tones such that they are at least a half-octave below the patient's tinnitus frequency.

13. The system of claim 1, wherein:
the sound generator is a headphone.

14. A system for treating tinnitus comprising:
a clinical controller executing tinnitus therapy software;
a vagus nerve stimulation (VNS) implantable pulse generator (IPG) in communication with the clinical controller and receiving stimulation signals from the clinical controller;
a VNS lead connected to the VNS IPG;
a VNS electrode connected to the VNS lead and receiving stimulation signals through the VNS lead from the VNS IPG; and
a sound generator connected to the clinical controller, wherein the clinical controller plays selected sound files through the sound generator while sending stimulation signals to the VNS IPG such that respective selected sounds of respective sound files may be heard by a patient while a stimulation pulse train at the VNS electrode causes the patient's vagus nerve to be stimulated, wherein
the system is configured to receive input based on the patient's tinnitus frequency, and
the selected sounds are therapeutic tones, and wherein the system is configured to automatically play the therapeutic tones such that they are at least a half-octave below the patient's tinnitus frequency.

15. The system of claim 14, wherein the clinical controller is a laptop computer.

16. The system of claim 14, wherein the VNS IPG receives stimulation parameters from the clinical controller.

17. The system of claim 14, wherein the selected sounds are therapeutic tones, and wherein the system is configured to execute a session that automatically applies at least 100 therapeutic tones per day.

18. The system of claim 14, wherein the selected sounds are therapeutic tones, and wherein the system is configured to execute a session that automatically applies at least 300 therapeutic tones per day.

19. The system of claim 14, wherein the selected sounds are therapeutic tones, and wherein the system is configured to play each therapeutic tone such that each therapeutic tone has a duration of about 500 milliseconds.

20. The system of claim 14, wherein the selected sounds are therapeutic tones, and wherein the system is configured to execute a session that repetitively plays each of the plurality of therapeutic tones in a temporally random manner.

21. The system of claim 14, wherein the selected sounds are therapeutic tones, and wherein the system is configured to execute a session that repetitively plays each of the plurality of therapeutic tones in a frequency-based random manner.

22. The system of claim 14, wherein the selected sounds are therapeutic tones, and wherein the system is configured to execute a session that plays each therapeutic tone such that it is a pure tone.

23. The system of claim 14, wherein the selected sounds are therapeutic tones, and wherein the system is configured to shape the therapeutic tones with a ramp function.

24. The system of claim 14, wherein the selected sounds are therapeutic tones, and wherein the system is configured to encode the therapeutic tones with location data.

25. The system of claim 14, wherein the selected sounds are therapeutic tones, and wherein the system is configured to automatically play the therapeutic tones such that they are at least a half-octave above the patient's tinnitus frequency.

26. The system of claim 14, wherein:
the sound generator is a headphone.

* * * * *